(12) United States Patent
Kopp

(10) Patent No.: US 12,403,217 B2
(45) Date of Patent: Sep. 2, 2025

(54) BIODEGRADEABLE IMPLANT COMPRISING COATED METAL ALLOY PRODUCT

(71) Applicant: Karl Leibinger Asset Management Gmbh & Co. KG, Mühlheim (DE)

(72) Inventor: Alexander Kopp, Aachen (DE)

(73) Assignee: KARL LEIBINGER ASSET MANAGEMENT GMBH & CO. KG, Muhlheim (DE)

( * ) Notice: Subject to any disclaimer, the term of this patent is extended or adjusted under 35 U.S.C. 154(b) by 1004 days.

(21) Appl. No.: 17/296,244

(22) PCT Filed: Nov. 22, 2019

(86) PCT No.: PCT/EP2019/082226
§ 371 (c)(1),
(2) Date: May 23, 2021

(87) PCT Pub. No.: WO2020/104653
PCT Pub. Date: May 28, 2020

(65) Prior Publication Data
US 2022/0016315 A1  Jan. 20, 2022

(30) Foreign Application Priority Data
Nov. 23, 2018  (DE) .......................... 102018129604.5

(51) Int. Cl.
| | |
|---|---|
| *A61L 27/32* | (2006.01) |
| *A61L 27/30* | (2006.01) |
| *A61L 27/58* | (2006.01) |
| *C22C 18/00* | (2006.01) |
| *C22C 23/00* | (2006.01) |
| *C25D 11/02* | (2006.01) |
| *C25D 11/30* | (2006.01) |
| *C25D 11/36* | (2006.01) |

(52) U.S. Cl.
CPC ............. *A61L 27/32* (2013.01); *A61L 27/306* (2013.01); *A61L 27/58* (2013.01); *C22C 18/00* (2013.01); *C22C 23/00* (2013.01); *C25D 11/024* (2013.01); *C25D 11/026* (2013.01); *C25D 11/30* (2013.01); *C25D 11/36* (2013.01); *A61L 2420/02* (2013.01); *A61L 2430/02* (2013.01)

(58) Field of Classification Search
CPC ........ A61L 27/32; A61L 27/306; A61L 27/58; A61L 2420/02; A61L 2430/02; A61L 31/028; A61L 31/086; A61L 31/088; A61L 31/148; A61L 27/047; C22C 18/00; C22C 23/00; C25D 11/024; C25D 11/026; C25D 11/30; C25D 11/36
See application file for complete search history.

(56) References Cited

U.S. PATENT DOCUMENTS

| | | | |
|---|---|---|---|
| 8,828,215 B2 | 9/2014 | Blawert | |
| 2005/0079088 A1* | 4/2005 | Wirth | ................... A61L 31/022 |
| | | | 420/405 |
| 2012/0150295 A1* | 6/2012 | Dingeldein | ........... A61L 31/148 |
| | | | 205/333 |

FOREIGN PATENT DOCUMENTS

| | | |
|---|---|---|
| DE | 102016007176 A1 | 6/2016 |
| EP | 2545945 A2 | 1/2013 |
| WO | 2012007181 A1 | 1/2012 |

OTHER PUBLICATIONS

Li et al., Scientific Reports, vol. 5, No. 10719, 2015 (Year: 2015).*
Echeverry-Rendon, et al.; "Improved corrosion resistance of commercially pure magnesium after its modification by plasma electrolytic oxidation with organic additives", Journal of Biomaterials Applications 2018, vol. 33(5) 725-740, DOI: 10.1177/0885328218809911.
Applicant: Meotec GmbH & Co. KG; Application No. 10 2018 129 604.5; German Office Action; dated Apr. 2, 2019; 5 pgs.
S. V. Gnedenkov, et al.; "Formation of Bioactie Anticorrosion Coatings on Resorbable Implants by Plasma Electrolytic Oxidation"; ISSN 2070-2051; Protection of Metals and Physical Chemistry of Surfaces, 2013, vol. 49, No. 7, pp. 874-879.; Jul. 3, 2012; 8 pgs.; DOI: 10.1134/S2070205113070071.
Pan, Yk; [ et al.]: Effects of phosphates on microstructure and bioactivity of micro-arc oxidized calcium phosphate coatings on Mg-Zn-Zr magnesium alloy. In: Colloids and Surfaces B: Biointerfaces, 2013, vol. 109, pp. 1-9. E-ISSN 1873-4367.
Chen, S; [ et al.]: In vivo degradation and bone response of a composite coating on Mg-Zn-Ca alloy prepared by microarc oxidation and electrochemical deposition. In: Journal of biomedical materials research Part B - Applied Biomaterials, 2012, vol. 100B, pp. 533-543. E-ISSN 1552-4981.
Lee, Km; [ et al.]: Electrochemical reaction of ZrOZ-incorporated oxide layer on AZ91 Mg alloy processed by plasma electrolytic oxidation. In: Surface and Coatings Technology, 2011, vol. 205, pp. 3779-3784. E-ISSN 1879-3347.
Matykina, E; [ et al.]: Role of PEO coatings in long-term biodegradation of a Mg alloy. In: Applied Surface Science, 2016, vol. 389, pp. 810-823. E-ISSN 1873-5584.
Mohedano, M; [ et al.]: Role of particle type and concentration on characteristics of P'EO coatings on AM 50 magnesium alloy. In: Surface & Coatings Technology, 2018, vol. 334, pp. 328-335. E-ISSN 1879-3347 (available online Nov. 23, 2017) https://doi.org/10.1016/j.surfcoat.2017.11.058.

(Continued)

Primary Examiner — Lezah Roberts
Assistant Examiner — Abdulrahman Abbas
(74) Attorney, Agent, or Firm — Tarolli, Sundheim, Covell & Tummino LLP

(57) ABSTRACT

The invention relates to a biodegradable implant comprising a surface coated magnesium alloy or zinc alloy product, whereby the coating layer comprises oxides and/or phosphates of from rare-earth elements, Mg, Ca, Zn, Zr, Cu, Fe, Sr, Li, Mn or Ag wherein the coating is preferably generated by plasma electrolytically oxidation (PEO). The invention further comprises a method for preparing the coated magnesium or zinc alloy product of the implant.

18 Claims, 20 Drawing Sheets

(56) References Cited

OTHER PUBLICATIONS

Applicant: Karl Leibinger Asset Management Gmbh & Co. KG; Application No. 10 2018 129 604.5; Office Action dated Mar. 26, 2025; 16 pgs.

* cited by examiner

Ca K_ROI (28)

Fe K_ROI (10)

Ni K_ROI (14)

Zn K_ROI (12)

Zr K_ROI (8)

Fig. 8

Phase P K/MgK/ C K

| Element | Weight % | Atomic % |
|---|---|---|
| C K | 62.34 | 73.87 |
| O K | 17.98 | 16.00 |
| F K | 0.00 | 0.00 |
| MgK | 9.71 | 5.68 |
| AlK | 0.00 | 0.00 |
| P K | 9.37 | 4.30 |
| CaK | 0.15 | 0.05 |
| FeK | 0.06 | 0.01 |
| NiK | 0.04 | 0.01 |
| ZnK | 0.10 | 0.02 |
| ZrK | 0.25 | 0.04 |

Phase C K/MgK

| Element | Weight % | Atomic % |
|---|---|---|
| C K | 62.34 | 73.87 |
| O K | 17.98 | 16.00 |
| F K | 0.00 | 0.00 |
| MgK | 9.71 | 5.68 |
| AlK | 0.00 | 0.00 |
| P K | 9.37 | 4.30 |
| CaK | 0.15 | 0.05 |
| FeK | 0.06 | 0.01 |
| NiK | 0.04 | 0.01 |
| ZnK | 0.10 | 0.02 |
| ZrK | 0.25 | 0.04 |

Phase: Unallocated

| Element | Weight % | Atomic % |
|---|---|---|
| C K | 61.23 | 78.68 |
| O K | 12.88 | 12.43 |
| F K | 0.44 | 0.36 |
| MgK | 6.81 | 4.32 |
| AlK | 0.45 | 0.26 |
| P K | 0.05 | 0.02 |
| CaK | 1.73 | 0.66 |
| FeK | 2.04 | 0.57 |
| NiK | 1.61 | 0.42 |
| ZnK | 1.80 | 0.43 |
| ZrK | 10.96 | 1.85 |

Phase: MgK/P K/O K

| Element | Weight % | Atomic % |
|---|---|---|
| C K | 21.41 | 31.42 |
| O K | 37.29 | 41.09 |
| F K | 1.26 | 1.17 |
| MgK | 23.33 | 16.91 |
| AlK | 0.19 | 0.12 |
| P K | 16.12 | 9.17 |
| CaK | 0.08 | 0.04 |
| FeK | 0.06 | 0.02 |
| NiK | 0.02 | 0.01 |
| ZnK | 0.05 | 0.01 |
| ZrK | 0.17 | 0.03 |

| Phase C K/MgK/ P K/O K | | |
|---|---|---|
| Element | Weight % | Atomic % |
| C K | 77.47 | 83.50 |
| O K | 16.73 | 13.54 |
| F K | 0.46 | 0.32 |
| MgK | 4.01 | 2.14 |
| AlK | 0.07 | 0.03 |
| P K | 1.00 | 0.42 |
| CaK | 0.08 | 0.02 |
| FeK | 0.05 | 0.01 |
| NiK | 0.01 | 0.00 |
| ZnK | 0.02 | 0.00 |
| ZrK | 0.10 | 0.01 |

| Phase MgK | | |
|---|---|---|
| Element | Weight % | Atomic % |
| C K | 7.09 | 13.42 |
| O K | 1.06 | 1.54 |
| F K | 0.00 | 0.00 |
| MgK | 89.53 | 83.68 |
| AlK | 0.62 | 0.53 |
| P K | 0.59 | 0.43 |
| CaK | 0.22 | 0.13 |
| FeK | 0.04 | 0.02 |
| NiK | 0.02 | 0.01 |
| ZnK | 0.48 | 0.17 |
| ZrK | 0.32 | 0.08 |

Spectrum for Phase : P K/MgK/C K

EDS spot selection

Spot 1

| Element | Weight % | Atomic % |
|---|---|---|
| C K | 8.77 | 14.08 |
| O K | 42.05 | 50.68 |
| F K | 0.60 | 0.61 |
| Mg K | 26.66 | 21.14 |
| Al K | 0.10 | 0.07 |
| P K | 21.31 | 13.26 |
| Ca K | 0.11 | 0.05 |
| Fe K | 0.08 | 0.03 |
| Ni K | 0.06 | 0.02 |
| Zn K | 0.07 | 0.02 |
| Zr K | 0.19 | 0.04 |

Spot 2

| Element | Weight % | Atomic % |
|---|---|---|
| Mg K | 98.28 | 99.31 |
| Ca K | 0.47 | 0.29 |
| Zn K | 0.58 | 0.22 |
| Zr K | 0.67 | 0.18 |

WE43-PEO: EDS spot selection

Spot 1

| Element | Weight % | Atomic % |
|---|---|---|
| C K | 9.35 | 14.96 |
| O K | 43.59 | 52.35 |
| F K | 0.48 | 0.49 |
| Mg K | 24.82 | 19.62 |
| Al K | 0.14 | 0.10 |
| P K | 19.43 | 12.05 |
| Zr L | 1.22 | 0.26 |
| Nd L | 0.49 | 0.06 |
| Fe K | 0.06 | 0.02 |
| Y K | 0.43 | 0.09 |

Spot 2

| Element | Weight % | Atomic % |
|---|---|---|
| Mg K | 93.84 | 98.48 |
| Y L | 3.39 | 0.97 |
| Zr L | 0.54 | 0.15 |
| Nd L | 2.22 | 0.39 |

BIODEGRADEABLE IMPLANT COMPRISING COATED METAL ALLOY PRODUCT

RELATED APPLICATIONS

The present invention is a U.S. National Stage under 35 USC 371 patent application, claiming priority to Serial No. PCT/EP2019/082226, filed on 22 Nov. 2019; which claims priority of DE 102018129604.5, filed on 23 Nov. 2018, the entirety of both of which are incorporated herein by reference.

FIELD OF THE INVENTION

The invention relates to a biodegradable implant comprising a surface coated magnesium alloy product. The invention further comprises a method for preparing the magnesium alloy product. The invention relates to a biodegradable implant comprising a surface coated zinc alloy product. The invention further comprises a method for preparing the zinc alloy product.

BACKGROUND OF THE INVENTION

Notably, Magnesium is the fourth most abundant cation in the human body, with an estimated 1 mol of magnesium stored in the body of a normal 70 kg adult, with approximately half of the total physiological magnesium stored in bone tissue. The presence of magnesium in the bone system is beneficial to bone strength and growth. Magnesium alloys have specific density (1.74-2 g/cm3) and Young's modulus (41-45 GPa) most close to those (1.8-2.1 g/cm3, 3-20 GPa) of human body's bone.

Zn is the second most abundant micronutrient in living organisms and is fundamental to cell biology, human anatomy, and physiology. It is necessary for hundreds of enzymatic reactions, affecting development, maturation, proper immune function, numerous disease states, and cancer. In humans, average daily zinc intake is 4-14 mg/day, and normal plasma levels range from 70 to 120 µg/dL, whereas plasma levels <60 µg/dL are considered low. Zn deficiency can be observed in growth failure, but Zn toxicity is rarely a concern as ingestion of ten times the recommended daily dose leads to few symptoms.

Therefore, in orthopedic and bone repairing or replacement applications magnesium or zinc alloys are particularly superior to any other metallic or polymer implants in terms of physical and mechanical properties, as the dissimilarity in Young's modulus between an implant and natural bone can result in stress shielding effects, leading to concentration of stress at the interface between the bone and implant reducing stimulation of new bone growth and decreasing implant stability.

Another major advantage of using magnesium or zinc and its alloys as implant materials, for instance for the fabrication of surgical implants, are their ability to biodegrade in situ. This in turn means that the implant does not remain in the body. A further surgery to remove the implant is not required and the risks associated with prolonged implant incorporation such as lack of patient compliance, allergies, inflammation, microgliding, particle abrasion, infections, arthrosis or osteopenia due to stress shielding are greatly reduced or abolished.

The in vivo degradation (also denominated as biodegradation) of Magnesium or Zinc and its alloys is associated with the generation of hydrogen which as a result can also form gas bubbles within the tissue. Without being restricted to a theory it is believed that this problem is caused by a too fast initial degradation process of the magnesium implant in vivo. The degradation rate of the magnesium but also zinc alloys seems to be too fast, in particular at the beginning directly after implantation. This results in the formation of gas bubbles or even gas pockets which could deteriorate the surrounding tissue. This is a major drawback of magnesium and zinc and actually hampers the broad application of magnesium or zinc based implants.

Even though Mg or Zinc and its alloys have been investigated as implants for almost two centuries, commercial implants containing Mg or Zn and its alloys showing favorable degradation behavior are still not available. Hereby, the advantages and obvious benefits from biodegradable metal implants impel the research of improved Mg alloy materials and the development of implantation devices derived from them.

However, the construction of optimized implants for tissue is hampered by the fact that Mg or Zn is a special lightweight metal that needs specific knowledge, careful professional handling and experience-based design to be a successful biomaterial.

In sum, a ready-to use implant should combine various complex requirements. At first it should represent a sufficiently stable support structure at the time of implantation but ideally is biodegradable so that the diminishing implant structures are substituted by the endogenous regenerating tissue/bone structures. Secondly, the materials and the structures build from it should enable a good substrate for the colonization, proliferation and/or differentiation of the biological cells. Thirdly, the materials should be non-toxic and non-immunogenic. Fourthly, the implant should be usable in different pathological situations enabling the regeneration of different tissues. The prior art implants do only partially fulfill these needs and have their disadvantages in one or more of the requirements.

Hence, there is still a need for an improved magnesium or zinc based implant. The objective of the present invention thus is to provide a biodegradable magnesium or zinc based implant which overcomes at least one of the above mentioned disadvantages.

This problem is solved by provision of a biodegradable implant according to claim 1. Specific embodiments are subject matter of further independent claims.

SUMMARY OF THE INVENTION

In a first aspect the present invention provides a biodegradable implant comprising a magnesium or zinc alloy product coated on its surface with a coating layer comprising at least two substances being
  a. a metal oxide of a metal selected from rare elements, Mg, Ca, Zn, Zr, Cu, Fe, Sr, Li, Mn or Ag; and/or
  b. a metal phosphate of a metal selected from rare elements, Mg, Ca, Zn, Zr, Cu, Fe, Sr, Li, Mn or Ag.

The implant of the present invention has several advantages over implant devices known in the prior art.

The coating of the invention establishes a further dimension of magnesium or zinc device modification beside the well-established variation of the alloy composition.

It thus adds a further variable when preparing metal alloy implants and can be combined with the established Mg or Zn alloys.

The coated magnesium or zinc alloys are both non-toxic and non-immunogenic and have thus have the sufficient safety profile.

Notably, the magnesium or zinc alloy does not require the use of aluminium, one of the most common alloy components of Magnesium alloys (see e.g. AZ31/AZ91 or Zn-4Al-1Cu). Aluminium is a neurotoxic metal and which may be the single most aggravating and avoidable factor related to Alzheimer's Disease.

Due to their mixed metal phosphate/oxide coating they exhibit an in vivo-degradation rate which is in the clinical relevant range, e.g. being on one side fast enough to be substituted by the regrowing tissue/bone and on the other side being not too fast to result in hydrogen gas bubbles or pockets.

Furthermore, the coated magnesium or zinc alloy of the invention exhibited a degradation rate with a lower standard deviation which therefore has a better predictability. This allows shorter development cycles and reduces testing in animal models.

Furthermore, the surface coating increases the surface hardness of the material allowing the use for implant structures that have to resist considerable mechanical stress such as screws, plates, wedges, pins, anchors or nails.

During degradation the Mg or Zn reacts with water to yield the strong base magnesium or zinc hydroxide. The inventors could further show that the coated magnesium or zinc alloy products of the invention show during in vivo degradation only a moderate increase in pH value which was well within the physiological range of 7 to 8.

A further advantage of Magnesium or Zinc as implant material is the fact, that magnesium is a natural component of the body and furthermore has many important functions within the body. Hereby, its biodegradation leads to generation of $Mg^{2+}$ or $Zn^{2+}$ cations which are beneficial for several cell types, especially nerve cells.

As the inventors found out the coated mg or zinc alloy can be prepared by plasma electrolytically oxidation (PEO), a process that can be performed also in industrial scale.

Furthermore, the PEO coating method enables the coating of delicate structures with complex interior geometry.

Since the implant device of the invention can be based on known magnesium or zinc alloys, it can be easily produced in a cost efficient manner.

DETAILED DESCRIPTION OF THE INVENTION

According to the invention, the coating layer comprises at least two and preferably at least three substances of the listed two substance classes, namely a first substance class of phosphates and a second substance class of oxides. Accordingly, the coating layer comprises three, four five six, seven eight, nine, ten or even more of the listed substances.

In a preferred embodiment, the coating layer comprises exactly three substances, which are accordingly one metal oxide and two metal phosphate compounds based on the listed metals.

In a preferred embodiment, the coating layer comprises exactly three substances, which are accordingly two metal oxides and one metal phosphate compound based on the listed metals.

In one embodiment of the invention, the metal oxide or metal phosphate forms a crystalline domain within the coating layer. In a preferred embodiment the coating layer is a layer with a crystal content of more than 10%, preferably with more than 20% crystal content, more preferably with more than 30% crystal content and especially with more than 50% crystal content.

In an alternative embodiment of the invention, the metal oxide or metal phosphate forms an amorphous domain within the coating layer. In a preferred embodiment the coating layer is an amorphous layer. Hereby, the term "amorphous layer" is defined as a layer with less than 5% crystal content, preferably with less than 2% crystal content, more preferably with less than 1% crystal content and especially with less than 0.5% crystal content.

In a preferred embodiment the coating layer consists of at least 2 or more sublayers, which can be separated by analytical measurements of the phase composition or crystalline content. Alternatively, the sublayer show visible features to distinguish between the different layers. The transition from one to another sublayer can either be determined by discrete or gradual differences in crystalline contents, phase composition or visible features. While at least one of the layers shows no or only a low content of crystalline domains, the second and every following sublayer exhibits a subsequently higher content of crystalline domains, a specific phase composition or a visible feature than the prior one. The order of those specific properties can go in both directions of the layer, e.g. the sublayer with the lowest content of crystalline domains, a specific phase composition or visible feature can either be located at the interface to the base material or the outer surface of the implant, being in contact with the surrounding tissue. A visible feature can be porosity, specific defects, visible precipitations or any other kind of specific visible aspect that be distinguished by its appearance.

In one embodiment the coating layer has a thickness of between 2 to 50 μm, preferably 5 to 35 μm, particularly preferably of between 8 to 24 μm and especially of between 12 to 18 μm.

In a further embodiment, the coating layer comprises metal fluorides which increase in their concentration starting from the top surface of the coating layer down to the bottom, alloy-product oriented surface of the coating layer, building preferably a distinct metal fluoride enriched zone at the bottom surface of the coating layer.

In a preferred embodiment, the coating layer has two fluoride enriched zones, which are at the bottom surface of the oxide sublayer and the top surface of the oxide sublayer. The oxide sublayer does constitute the bottom layer of the coating layer sitting directly on top of the alloy surface.

The top surface of the coating layer has a mean Vickers hardness from 150 to 800, preferably from 200 to 600, and more preferably from 250 to 400, as measured according DIN EN ISO 6507-1/4:2018.

The coating layer comprises at least two sub layers being a bottom barrier layer located towards the alloy-product and a porous top layer.

In a preferred embodiment the rare-earth elements (RE) as metal part of the oxides/phosphates of the coating layer are selected from the list consisting of Yttrium (Y), Scandium (Sc), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb) and Lutetium (Lu) including any combination thereof.

In a preferred embodiment of the invention, the coating layer is generated by plasma electrolytic oxidation (PEO).

In another embodiment the coating layer of the magnesium alloy or zinc product is a porous layer, which preferably has a porosity of 2 to 50%, more preferably of between 3 to 25%, and particularly preferable of 4 to 12%. The pores allow the body fluid to reach the magnesium or zinc alloy as inner product material which then starts to degrade by generating magnesium or zinc hydroxide and hydrogen. Furthermore, the pores allow an ingrowth of the neighboring tissue allowing a better inclusion of the implant.

In one embodiment, the coating layer is designed with a channel network which gives the layer a porosity. Preferably, the channel network is designed with openings which face towards the surface of the coating layer and whose respective surface cross-sectional diameters are less than the respective channel depth. The channels of the channel network can extend in the direction of depth of the coating layer, or in the radial direction. The channel branches or channel parts can be straight and/or curved.

In a preferred embodiment, the channel network comprises contiguous channel branches which extend through at least the greater part of the layer as seen in cross section.

In a preferred embodiment, the channels of the network are mainly connected to each other.

In complementary embodiment, the channels of the network are mainly not connected to each other.

The channel network generally provides a good substrate for ingrowth of cells and tissues. This ingrowth might be further enhanced by prefilling the channel network with bioactive compound such as bone-growth initiating or -stimulating substances.

In an alternative embodiment, the coating layer is devoid of a channel network.

Preferably, the pores at the top surface of the coating layer have a mean pore size of between 0.1 $\mu m^2$ to 10 $\mu m^2$, preferably of 2 $\mu m^2$ to 8 $\mu m^2$, particularly preferably of 4 $\mu m^2$ to 6 $\mu m^2$.

In one embodiment the magnesium alloy of the product is a Mg—Y-RE-Zr alloy and preferably a Mg—Y—Nd—Zr alloy, which is also known as WE43 alloy. Especially the rare-earth (RE) elements Dy, Y, Nd and Gd have minor toxicity and are beneficial to enhance the mechanical and corrosion properties. Due to excellent properties, e.g. relatively slow degradation in aqueous solutions and good electrochemical properties accompanied by excellent mechanical properties, the WE43 alloy is the most preferred Mg alloy.

In one embodiment, the magnesium alloy is a Mg—Y—Nd alloy with or without addition of Zr. In a preferred embodiment the magnesium alloy has hereby an Yttrium content between 3 and 5% wt.-% and a Nd content between 2 and 4% wt.-%.

In a further embodiment the mg alloy comprises Calcium and Zink, preferably Mg—Ca—Zn or Mg—Zn—Ca with or without addition of Zr, even more preferably with Ca and Zn contents each below 1 wt.-% or below 2 wt.-% or below 5 wt.-%.

In one embodiment, the zinc alloy is a Zn—Mg alloy with or without addition of Zr. In a preferred embodiment the zinc alloy has hereby a magnesium content between 0.1 and 5% wt.-%, preferably 0.15 and 2% wt.-%, most preferably 0.2 and 1% wt.-%.

In a further embodiment the Zn alloy further comprises Calcium and is a Zn—Mg—Ca or Zn—Ca—Mg alloys with Ca contents between 0.1 and 5% wt.-%, preferably 0.15 and 2% wt.-%, most preferably 0.2 and 1% wt.-%.

In a further embodiment the Zn alloy further comprises Silver with or without the addition of magnesium and is a Zn—Mg, Zn—Mg—Ag or Zn—Ag—Mg alloy with Ag contents between 0.1 and 8% wt.-%, preferably 0.5 and 3% wt.-%, most preferably 1.0 and 1.5% wt.-% and magnesium contents between 0.1 and 5% wt.-%, preferably 0.15 and 2% wt.-%, most preferably 0.2 and 1% wt.-%.

In a further embodiment the Zn alloy further comprises Copper with or without the addition of magnesium and is a Zn—Cu, Zn—Mg—Cu or Zn—Cu—Mg alloy with Ag contents between 0.1 and 8% wt.-%, preferably 0.5 and 3% wt.-%, most preferably 1.0 and 1.5% wt.-% and copper contents between 0.1 and 5% wt.-%, preferably 0.15 and 2% wt.-%, most preferably 0.2 and 1% wt.-%.

In a further embodiment the Zn alloy further comprises Strontium with or without the addition of magnesium and is a Zn—Sr, Zn—Mg—Sr or Zn—Sr—Mg alloy with Sr contents between 0.05 and 2% wt.-%, preferably 0.1 and 1% wt.-%, most preferably 0.2 and 0.8% wt.-% and magnesium contents between 0.1 and 5% wt.-%, preferably 0.15 and 2% wt.-%, most preferably 0.2 and 1% wt.-%.

In a further embodiment the Zn alloy further comprises Lithium with or without the addition of magnesium and is a Zn—Li, Zn—Li—Mg or Zn—Mg—Li alloy with Li contents between 0.05 and 2% wt.-%, preferably 0.1 and 1% wt.-%, most preferably 0.2 and 0.8% wt.-% and magnesium contents between 0.1 and 5% wt.-%, preferably 0.15 and 2% wt.-%, most preferably 0.2 and 1% wt.-%.

In a further embodiment the Zn alloy further comprises Manganese with or without the addition of magnesium and is a Zn—Li, Zn—Li—Mg or Zn—Mg—Li alloy with Li contents between 0.05 and 2% wt.-%, preferably 0.1 and 1% wt.-%, most preferably 0.2 and 0.8% wt.-% and magnesium contents between 0.1 and 5% wt.-%, preferably 0.15 and 2% wt.-%, most preferably 0.2 and 1% wt.-%.

In a further embodiment the coating layer of the surface coated magnesium or zinc alloy product comprises a coating layer essentially consisting of the elements Magnesium or Zinc, Oxygen and Phosphor, relating to a mixed Mg or Zn oxide/Mg or Zn phosphate layer.

In one embodiment, the coated magnesium or zinc alloy product of the invention has a hydrogen gas evolution rate of less than 1.0 $ml/cm^2$, preferably of less than 0.6 $ml/cm^2$, more preferably of less than 0.2 $ml/cm^2$, and even more preferably of less than 0.1 $ml/cm^2$, as measured by continuous volumetric measurement of the generated hydrogen gas after incubation for 100 hours in Minimal Essential Medium (MEM) at 37° C. under non-turbulent stirring. Due to this reduction in hydrogen generation as compared to Mg implants of the prior art, the implant of the invention possesses enhanced tissue compatibility and safety since the generation of gas bubbles or pockets is greatly diminished.

In a second aspect, the invention relates to a method for generating a coating layer on the surface of a magnesium or zinc alloy product by plasma electrolytic oxidation (PEO).

Plasma electrolytic oxidation (PEO), also known as Micro Arc Oxidation (MAO), is a promising novel process which has the capacity of fabricating a stable and adherent oxide layer on metals, such as Mg or Zn. This process is based on the anodic oxidation of the metal when connected to the high-voltage source which has been immersed in a proper electrolyte.

Plasma Electrolytic Oxidation (PEO) is a technique used to produce a hard, wear and corrosion resistant coating on valve metals, such as aluminium, titanium, magnesium and their alloys. The PEO process was developed from conventional anodising, although a higher voltage and a proper electrolyte is used. The characterising feature of PEO processes is the generation of small, short-lived micro discharges (plasma channels) on a treated metal surface, which convert the metal surface into a hard, oxide containing layer. The PEO process is carried out in environmentally friendly electrolytes, which do not contain chromates. Additionally, a high throwing power (the ability to deposit a coating uniformly on an irregular shaped metal) is another advantage of the process.

During PEO, several processes are taking place, such as formation of an oxide layer, dielectric breakdown, gas evolution and dissolution of the metal. The coating formation is dependent on the type of power supply, the solution used and the substrate.

In a preferred embodiment the method for generating a coating layer on the surface of a magnesium or zinc alloy product, comprising the following steps:
(i) Providing an aqueous electrolyte solution comprising an inorganic phosphate,
(ii) subjecting a magnesium or zinc alloy product to the aqueous electrolyte solution so that the surface of the magnesium alloy product which is to be treated is immersed in the electrolyte solution,
(iii) applying a voltage difference between the magnesium or zinc alloy product and a second electrode positioned in the aqueous electrolyte system for generating a plasma electrolytic oxidation on the immersed surface of the magnesium or zinc alloy product,
(iv) so that the immersed surface is converted to a mixed oxide/phosphate film.

In a preferred embodiment, the electrolyte solution to be used in the PEO process (also called "PEO-electrolyte solution") comprises an inorganic phosphate which is preferably selected from the list consisting of phosphoric acid, $Na_3PO_4$, $Na_4P_2O_7$, $Na_5P_3O_{10}$, $Na_6P_6O_{18}$, $Na_2HPO_4$, $NaH_2PO_4$, and $K_2P_2O_7$.

The inorganic phosphate is preferably contained within the aqueous electrolyte solution in a concentration of between 1 and 250 g/L, preferably between 10 and 100 g/L and even more preferably 45 and 65 g/L.

The aqueous PEO-electrolyte solution comprises in addition to an inorganic phosphate one or more alkaline compounds, which are preferably selected from the list consisting of potassium hydroxide, lithium hydroxide, sodium hydroxide and ammonium hydroxide.

The alkaline compound is preferably contained within the aqueous electrolyte solution in a concentration of between 1 and 250 g/L, preferably between 10 and 100 g/L and even more preferably 35 and 75 g/L.

The aqueous PEO-electrolyte solution further comprises one or more additives selected from hydrogen fluoride, urotropin and boric acid.

The additive is preferably contained within the aqueous electrolyte solution in a concentration of between 1 and 400 g/L, preferably between 25 and 350 g/L and even more preferably 30 and 80 g/L In another embodiment, the biodegradable implant comprising a magnesium or zinc alloy product is coated on its surface with a coating layer comprising at least three substances being a metal oxide of a metal selected from rare-earth elements, Mg, Ca, Zn, Zr, Cu, Fe, Sr, Li, Mn or Ag or a metal phosphate of a metal selected from rare-earth elements, Mg, Ca, Zn, Zr, Cu, Fe, Sr, Li, Mn or Ag.

In another preferred embodiment, the biodegradable implant comprising a magnesium or zinc alloy product is coated on its surface with a coating layer comprising at least three substances being at least one metal oxide of a metal selected from rare-earth elements, Mg, Ca, Zn, Zr, Cu, Fe, Sr, Li, Mn or Ag and two metal phosphates of a metal selected from rare-earth elements, Mg, Ca, Zn, Zr, Cu, Fe, Sr, Li, Mn or Ag.

In another preferred embodiment, the biodegradable implant comprising a magnesium or zinc alloy product is coated on its surface with a coating layer comprising at least three substances being at least two metal oxides of a metal selected from rare-earth elements, Mg, Ca, Zn, Zr, Cu, Fe, Sr, Li, Mn or Ag and one metal phosphate of a metal selected from rare-earth elements, Mg, Ca, Zn, Zr, Cu, Fe, Sr, Li, Mn or Ag.

In a preferred embodiment, the voltage as applied in the PEO method leads to an alternating current or voltage, preferably with a sinusoidal waveform.

In a preferred embodiment, the voltage as applied in the PEO method leads to an alternating pulsed current or voltage, also referred to as bipolar-pulsed.

In another preferred embodiment, the voltage as applied in the PEO method leads to a constant current or vice versa.

In a further preferred embodiment, the voltage or current as applied in the PEO method leads to an anodically pulsed current, also referred to as unipolar-pulsed.

In an even more preferred embodiment the pulsed currents or voltages are rectangular-shaped.

In an alternative embodiment the pulsed currents or voltages are sinusoidal-shaped or saw tooth-shaped.

In an alternative embodiment the pulsed currents or voltages are a superimposition of a rectangular and/or sinusoidal-shaped and/or saw tooth-shaped patterns.

In an alternative embodiment the biodegradable implant is manufactured by means of conventional manufacturing methods, such as casting, forming and subsequent subtractive manufacturing, such as turning, milling, grinding or similar.

In an alternative embodiment the biodegradable implant is manufactured by means of additive manufacturing methods, such as the Laser Powder Bed Fusion (LPBF), process also referred to as Selective Laser Melting or Selective Laser Sintering.

Therefore, a powder from a magnesium or zinc alloy is fabricated and subsequently fused by melting, sintering or other methods. Basically, every possible method to additively manufacture such an implant can be considered. As most of the processes change the microstructure of the implant, they also change the conditions for the creation of different oxides or phosphates according to the presented invention.

Specifically, a rectangular pulse form is used for the PEO coating process, whereby PEO coating process is performed with constant current.

In a further preferred embodiment, the applied frequency of pulses applied is between 1 and 5 kHz, preferably between 10 and 1.500 Hz, most preferably between 50 and 500 or between 100 and 1.000 Hz.

In a further embodiment, only a part of the biodegradable implant is coated.

In a further preferred embodiment, the whole surface of the biodegradable implant except the area contacted for the coating process is coated.

In a further preferred embodiment, the whole surface of the biodegradable implant is coated.

Plasma electrolytic oxidation (PEO), also known as Micro Arc Oxidation (MAO), is a promising novel process which has the capacity of fabricating a stable and adherent oxide layer on metals, such as Mg or Zn. This process is based on the anodic oxidation of the metal when connected to the high-voltage source which has been immersed in a proper electrolyte. The combination of the electrolyte solution has an effect on the stability of the passive layer, size and distribution of sparks and formed phases.

Plasma Electrolytic Oxidation (PEO) is a technique used to produce a hard, wear and corrosion resistant coating on valve metals, such as aluminium, titanium, magnesium and their alloys. The PEO process was developed from conventional anodising, although a higher voltage is used. The characterising feature of PEO processes is the generation of small, short-lived microdischarges (plasma channels) on a treated metal surface, which convert the metal surface into a hard, oxide layer. The PEO process is carried out in environmentally friendly electrolytes, which do not contain chromates. Additionally, a high throwing power (the ability to deposit a coating uniformly on an irregular shaped metal) is another advantage of the process.

During PEO, several processes are taking place, such as formation of an oxide layer, dielectric breakdown, gas evolution and dissolution of the metal. The coating formation is dependent on the type of power supply, the solution used and the substrate. Treatment parameters, such as current or voltage and time of the process, influence the coating formation and thus the properties of the coating. The complexity of the process and the number of influencing factors on the coating formation causes difficulties in process optimisation.

Examples (Magnesium)

For preparation of test pieces an extruded WE43 magnesium alloy bar with a diameter of 20.6 mm was cut into plates with a thickness of 1.5 mm. After treatment with an acidic activation solution (see below), the plates were installed into an electrolytic PEO-system immersed with different electrolyte solutions and subjected to PEO protocol.

The composition of the WE43 is as follows:
3.7-4.3% Yttrium
2.3-3.5% Rare-earth elements
0.1-0.6% Zirconium
Balance Magnesium The following electrolyte solutions were comparatively used in the PEO method:

| Electrolyte | Composition |
| --- | --- |
| E1 | Magnesium reference (WE 43) |
| E2 | Silicate and KOH |
| E3 | Silicate and KOH and Borate |
| E4 | Silicate and KOH and titanate |
| E5 | Silicate and KOH and borate and titanate |
| E6 | Phosphate and KOH |
| E7 | Phosphate and Ammonium hydroxide |
| E8 | Phosphate and KOH and aluminate |
| E9 | Phosphate and ammonium hydroxide and urea |
| E10 | Phosphate and ammonium hydroxide and EDTA |
| E11 | Phosphate and ammonium hydroxide and fluoride and urotropin |
| E12 | Phosphate and ammonium hydroxide and borate and fluoride and urotropin |

PEO treatment conditions were adapted individually for every test specimen in order to generate a thickness of the coating layer of 10±3.5 µm.

The following PEO parameters were applied:

| | |
| --- | --- |
| Activation of the test specimen | Incubate for 20 sec in an activation solution containing 2 g Oxalic acid-dihydrate in 100 ml aqua dest. followed by an incubation for 10 min in aqua dest. |
| Power source | Munk PSP family (Munk GmbH, Hamm, Germany) |
| Regulation | Constant current modus |
| Pulse form | Unipolar, rectangular |
| Frequency | 1,000 Hz |
| Current density | 1.6-4.9 A/dm$^2$ |
| (final) voltage | 400-500 V |
| Coating duration | 15-45 min |
| Electrolyte temp. | 12-21° C. |
| Stirring rate | 250 U/min |

The PEO was performed in an apparatus as schematically shown in FIG. 1. The test specimens as coated with the electrolyte solutions E1 to E12 (E1 is the uncoated negative control) were denominated as S1 to S12 and subjected to further analysis.

Analysis of the PEO Coated WE43 Test Specimen S1 to S12
1. Morphological Analysis In order to study the morphology of the distinct coating the test specimens were analyzed using scanning electron microscopy (SEM). Hereby the top surface of the coated test specimens was analyzed in top view or in a cross section view after cutting the test specimen. Exemplary pictures of the SEM analysis are shown in FIG. 2B.

2. EDS Spectra

The chemical composition of the coating layer was analyzed using energy-dispersive X-ray spectroscopy (EDS). The EDS spectrum for the probe S6 is shown in FIG. 2B (bottom right). In a more elaborated EDS analysis, a transverse section the PEO coated Magnesium alloy ZX00 was analyzed with EDS for the elemental composition. The results are shown in FIG. 5 in the form of so called live maps and in FIGS. 6 and 7 as element overlays. For five different phases the phase spectrum was collected and analyzed using the software TEAM™ Version V4.4.1 (AMETEK GmbH, Weiterstadt, Germany).

Hereby, the eZAF Smart Quant method was used which is an algorithm for quantification of an enhanced inclination range for up to 70 degrees for flat and polished probes. It includes corrections relating to the atomic number (=Z), absorption (=A) and fluorescence (=F).

The element distribution for these five phases are depicted in FIGS. 8 and 9. The EDS peaks are X-rays given off as electrons return to the K electron shell and were therefore specified with a "K" in the Figures.

Finally, a spot analysis was performed, whereby the cross section of the two PEO coated alloys ZX00 and WE43 were used to choose two spots, EDS spot 1 within the coating and EDS spot 2 within the Mg alloy product. The element distributions for these two spots were determined using eZAF Smart Quant. The element distribution for the PEO coated alloys ZX00 and WE 43 are depicted in FIGS. 10 and 11, respectively.

Notably, the presence of carbon is an artefact due to the probe preparation, since the probe is embedded in an epoxy resin and the freshly prepared surface will be contaminated with carbon containing compounds.

3. X-Ray Crystallography

The chemical composition of the PEO-coated Mg alloy was analyzed using X-ray crystallography using the diffractometer system XRD ID 3003 TT (Company GE Sensing & Inspection Technologies) Hereby, the Bragg-Brentano geometry (symmetrical) with Cu—K$_{alpha}$ radiation and 1D-detector and 0.03 °2theta step width was used. In a separate analysis, the following parameters were used: grazing incidence, (Omega-angels of 1, 3, 5 and 7°) with Cu—$K_{alpha}$ radiation secondary long Soller collimator and scintillation detector with 0.05 °2theta step width and 5 measuring time.

As shown in FIGS. 12 and 13, the Mg alloy-derived peaks with its hexagonal P36mmc structure dominate the spectrum. However, in the region between 39 and 45 2Theta, several peaks indicating the presence of $Mg_4Zn_7$ (monoklin MgZn crystal of space group C2/m) and one peak at 42.9 2Theta representing the MgO periclase (hexoctahedral crystal of space group Fm-3m) can be seen.

As shown in a separate analysis in FIGS. 14 and 15, the broad peak in the region between 20 and 35 2Theta shows that the coating consists of amorphous material.

4. Analysis of the Pore Size and Porosity

The SEM pictures of the surface of the test samples S2 to S12 were morphometrically analyzed by converting the picture with the software ImageJ (Wayne Rasband, USA) into the 8 bit format, followed by binarisation. After manually assigning a threshold for identification of pores, the pore size (i.e. the area of the pore given in $\mu m^2$) and the porosity in % were determined. The results are shown in FIG. 2A.

5. Analysis of the Hardness

The hardness of the test samples 51 to S12 was determined by micro hardness testing according to Vickers with a n=5 using the Fischerscope H100C apparatus (Helmut Fischer GmbH Sindelfingen) in the cross section of the test specimen. The Vickers hardness for S1 to S12 s shown in FIG. 2C. It can be seen, that the coating leads to an increased hardness of the Mg alloy products. Among the phosphate based electrolytes the order of hardness is at follows: S7>S6>S9~S10~S11>S12.

6. Analysis of the Degradability

The degradability of the test sample S11 in comparison to a non-coated WE43 Mg alloy product. was determined by volumetric analysis of the hydrogen gas which is generated during degradation. Hereby a test equipment according Hofstetter et al. ("Assessing the degradation performance of ultrahigh-purity magnesium in vitro and in vivo", Corrosion Science, 2015 (91): 29-36) was used. The test samples are incubated for 100 hours in Minimal Essential Medium (MEM) at 37° C. under non-turbulent stirring and the hydrogen gas evolution rate was measured by intermitted 12-hour interval volumetric measurement of the generated hydrogen gas. The degradation rates are shown in FIG. 16. Whereas the uncoated sample shows a steady increase up to 1.2 $ml/cm^2$ hydrogen after 100 hours, the PEO coated sample S11 leads to hydrogen amount of approx. 0.1 $ml/cm^2$.

7. Analysis of the Biocompatibility

For analysis of the in vitro toxicity of the coated test samples an in vitro test schema was applied which follows the norm DIN EN ISO 10993. This test scheme includes indirect testing by analysis of extracts and a direct testing. The testing was performed with the mouse fibroblast cell line L929.

7.1 Testing of Extracts

The indirect test was performed as follows:

Sterilisation of the test samples by immersion in isopropanol for 5 min. and drying in a sterile hood.

Generation of aqueous extracts by incubating the test samples S1 to S12 (n=2) for 72 hours with 3 ml of MEM cell culture medium under cell culture conditions (37° C., 5% $CO_2$, 95% humidity)

Centrifugation of the extracts at 14.000 U/min for 10 minutes to remove particles Plating of 100 µl CCL1 cells ($1 \times 10^5$ cells/ml) in a 96 well plate followed by incubation for 24 hours under cell culture conditions Addition of 100 µl extract (n=4 for each test sample) per well Incubation for further 24 hours Analysis of the cells using the BrdU, LDH and XTT tests The results are shown in FIG. 3. It can be seen that in the LDH test the samples S6 to S12 are similar in their effect to the negative control (NK) and thus show no apparent sign of toxicity. This correlates with the results from the TTX and BrdU tests showing that the probes S6 to S12 do not impair the cell viability as compared to the negative control NK.

7.2 Testing with Direct Contact

The direct test was performed as follows:

1 ml of the CCL1 cell suspension ($2.4 \times 10^5$ cells/ml) were plated on the probe specimen in a 24 well plates and incubated for 24 hours under cell culture conditions. Thereafter, the cells were analyzed using vital staining by addition of 2.5 mg fluorescein diacetate (FDA) and 3 µg propidium iodide (P1) and incubation for 3 minutes at room temperature. From each test sample 5 different positions of the probe body were analyzed using fluorescence microscopy.

As positive control a RM-Polyurethan plate with 1% zinc diethyldithiocarbamate (ZDEC) was used (Hatano Research Institute, Food and Drug Safety Center, Kanagawa, Japan). Negative controls were given by HDPE plastic sheet or a pure titan body grade 4 (Eutitan, Eukamed e.K., Essen). The pictures were analyzed by a multifactorial subjective scoring which was performed by three independent observers. Hereby the three effects "P1 positive cells", "rounded cells" and reduction of cell count" were quantified in four steps as depicted in the following table:

| | Manifestation (compared to negative control) | | | | |
|---|---|---|---|---|---|
| Effect | 0 | 1 | 2 | 3 | Significance |
| Reduction of cell number | No effect | Slight reduction | Median Reduction | Strong reduction | Cell growth |
| Rounded cells | No effect | Low number | Increased number | High number | Cell morphology |
| PI positive cells | No effect | Low number | Increased number | High number | Cell damage |

The cumulative scoring ranges from 0 depicting an excellent biocompatibility to 9 indicating a high cytotoxic potential. The mean score values are shown in FIG. 4. Hereby, the coated samples S10 and S11 show the best results.

Examples (Zinc)

For preparation of further test pieces an additively manufactured zinc alloy specimen with a diameter of 15 mm and 3 mm in height was used. After treatment with an acidic activation solution, the specimens were installed into an electrolytic PEO-system. The composition of the test piece was Zn1Mg (1 wt-% Magnesium, remainder is Zinc). An electrolyte solution containing Phosphates and KOH was utilized. PEO treatment conditions were adapted individually in order to generate a thickness of the coating layer of 10±3.5 µm. The following PEO parameters were applied:

| | |
|---|---|
| Power source | Munk PSP family (Munk GmbH, Hamm, Germany) |
| Regulation | Constant current modus |

| | |
|---|---|
| Pulse form | Unipolar, rectangular |
| Frequency | 1.500 Hz |
| Current density | 15-150 mA/cm$^2$ |
| (final) voltage | 350-500 V |
| Coating duration | 14 min |
| Electrolyte temp. | 18-21° C. |
| Stirring rate | 250 U/min |

The PEO was performed in an apparatus as schematically shown in FIG. 1. The test specimens as coated with the electrolyte solution are also depicted in FIGS. 17, 18 and 19.

BRIEF DESCRIPTION OF THE DRAWINGS

These and other aspects of the invention will be apparent from and elucidated with reference to the embodiments described hereinafter.

The invention will now be described, by way of example, based on embodiments with reference to the accompanying drawings.

In the drawings:

FIG. 1 shows a schematic drawing of a cell for PEO anodization.

Figure 2:
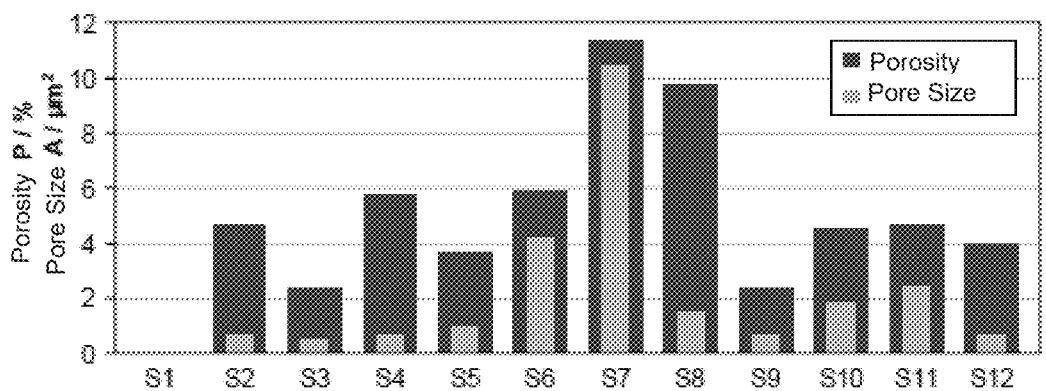
Figure 2:
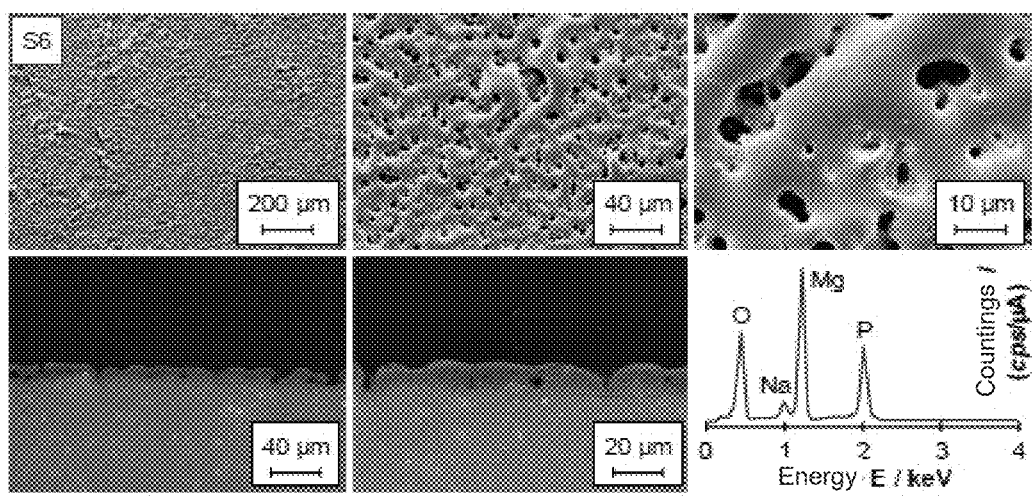
Figure 2:
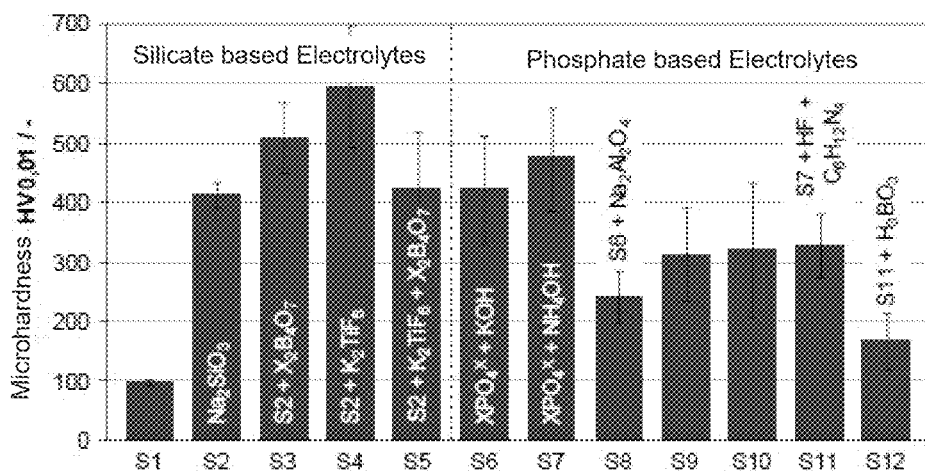

FIG. 2 A shows the results of the digital analysis of the coated test specimens S1 to S12 with regard to porosity (in %) and pore size (area of the pore in µm$^2$). In B the SEM pictures showing the surface morphology of the test sample S6 together with the EDS spectrum is shown.

Figure 3:
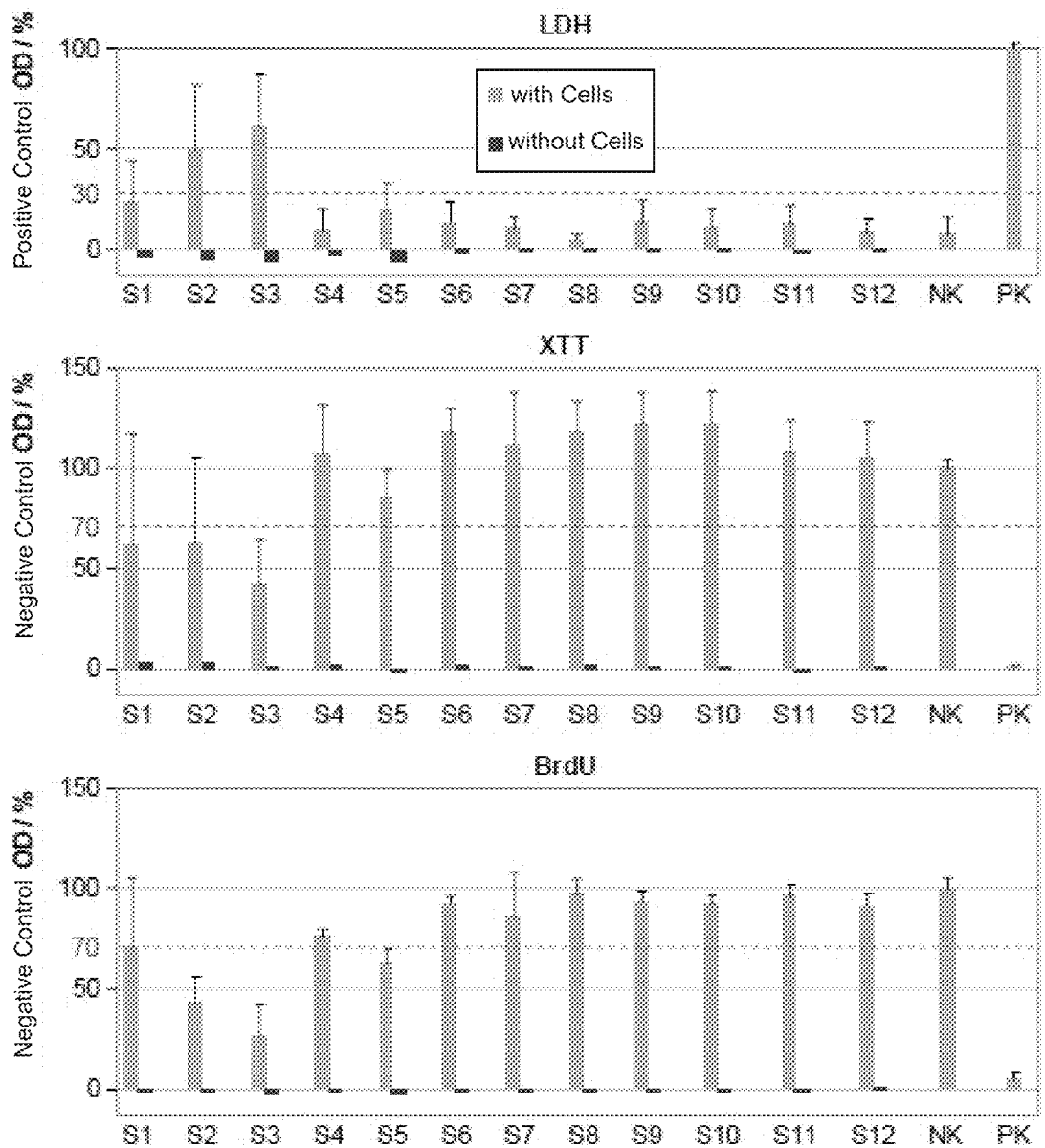

FIG. 3 shows the results for the LDH, XTT and BrdU testing of extracts taken from the test samples S1 to S12.

Figure 4:
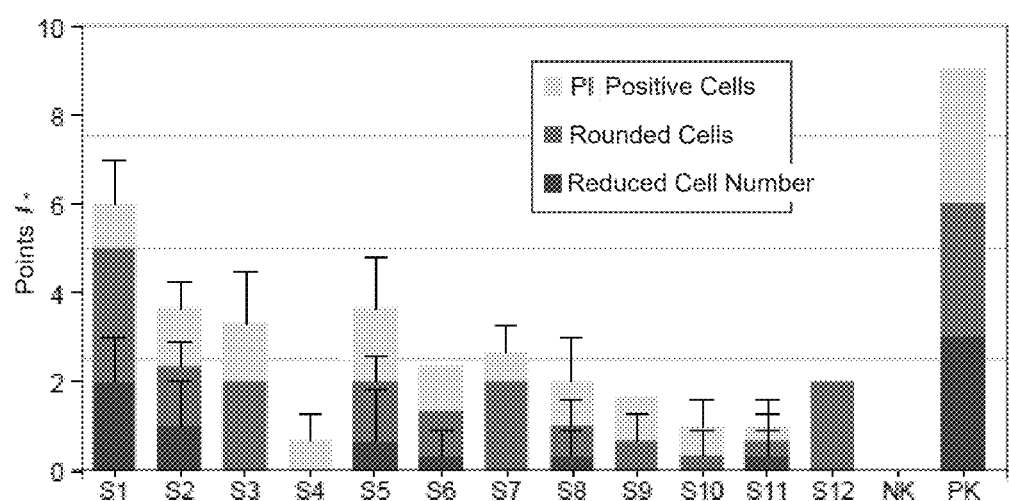

FIG. 4 shows the cumulative results of the in vitro toxicity testing of samples S1 to S12 including a negative control (NK) and a positive control (PK) after direct plating of CCL1 cells on the coated test samples S1 to S12.

Figure 5:
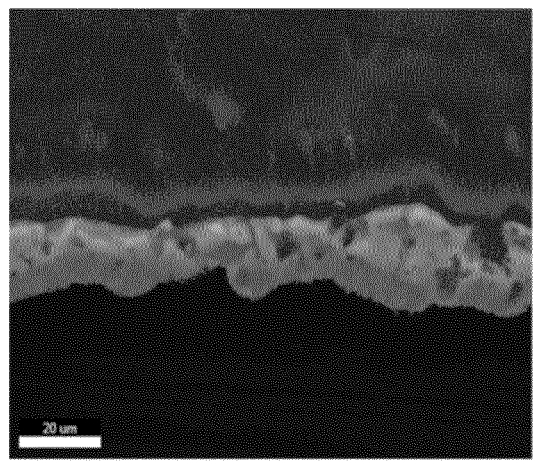
Figure 5:
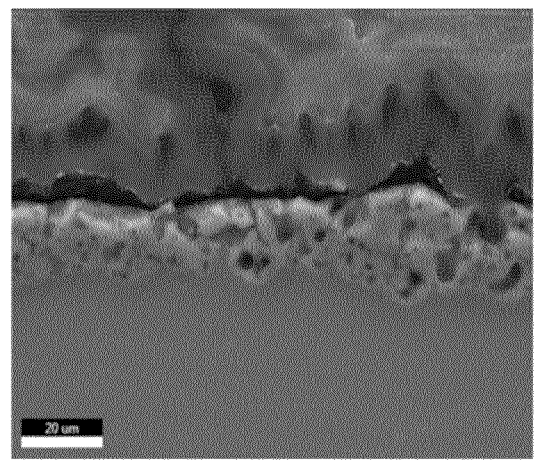
Figure 5:
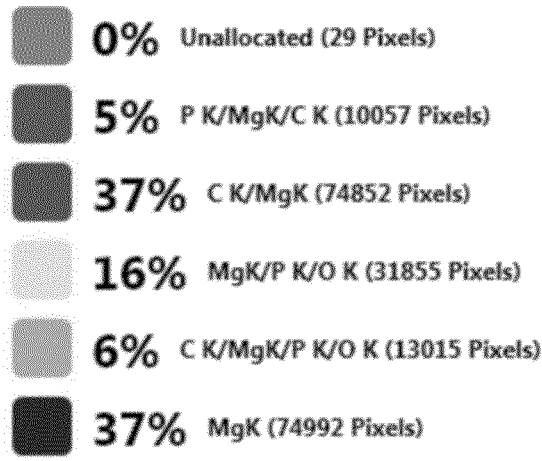
Figure 5:
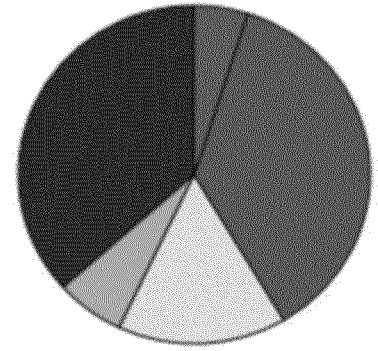

FIG. 5 shows the cross section of the PEO coated ZX00 Mg alloy in the SEM picture (right) and with a colour coded picture showing the distribution of the different coating phases as a so called live map (left). The figure legend for the color-coded phases with their elemental composition is shown in the bottom.

Figure 6:
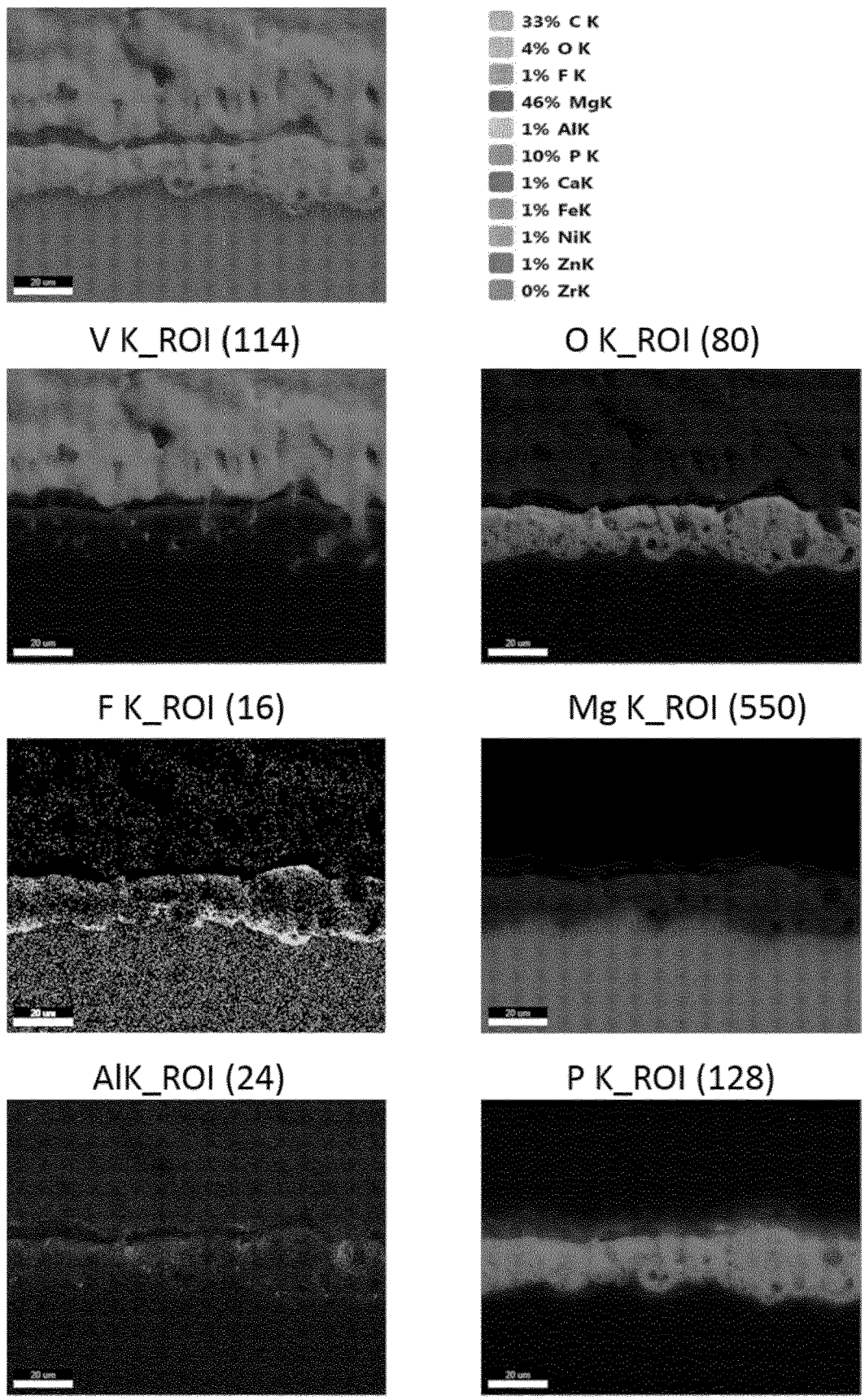

FIG. 6 shows the cross section of the PEO coated ZX00 Mg alloy with colour coded element overlays for all elements at top left with the element-colour allocation as depicted top right. In the following the separated element presentation for Fluor, Magnesium, Aluminium and Phosphor is shown.

Figure 7:
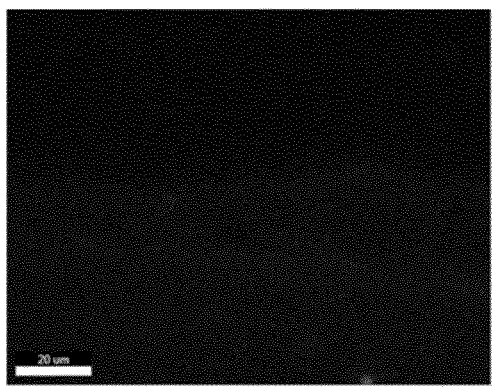
Figure 7:
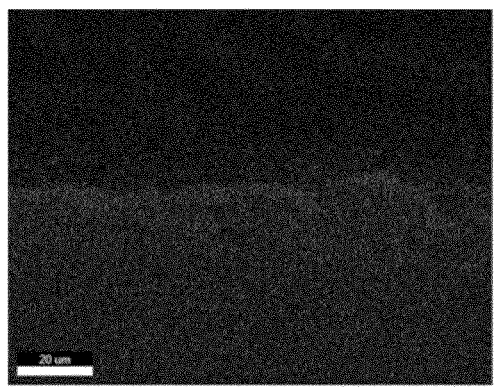
Figure 7:
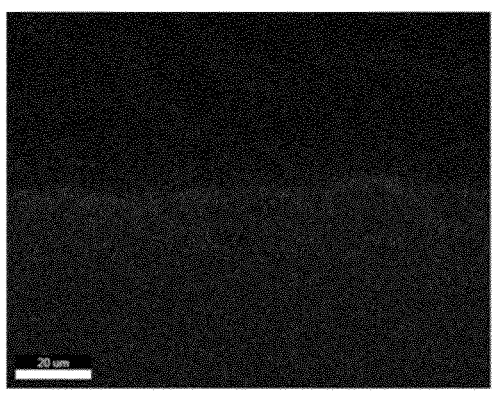
Figure 7:
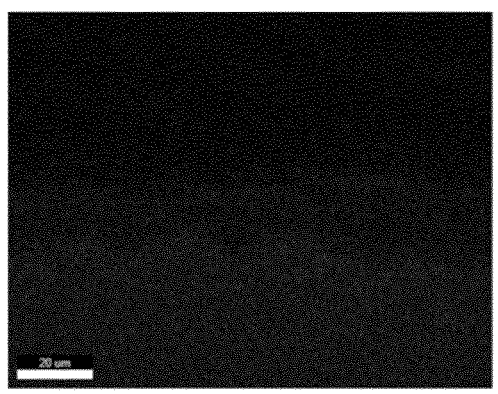
Figure 7:

FIG. 7 shows the cross section of the PEO coated ZX00 Mg alloy with colour coded separated element presentation for Calcium, Iron, Nickel, Zink and Zirconium.

FIG. 8 shows the results of the EDS analysis using eZAF Smart Quant for four different phases of the PEO coated Mg alloy ZX00.

Figure 9:
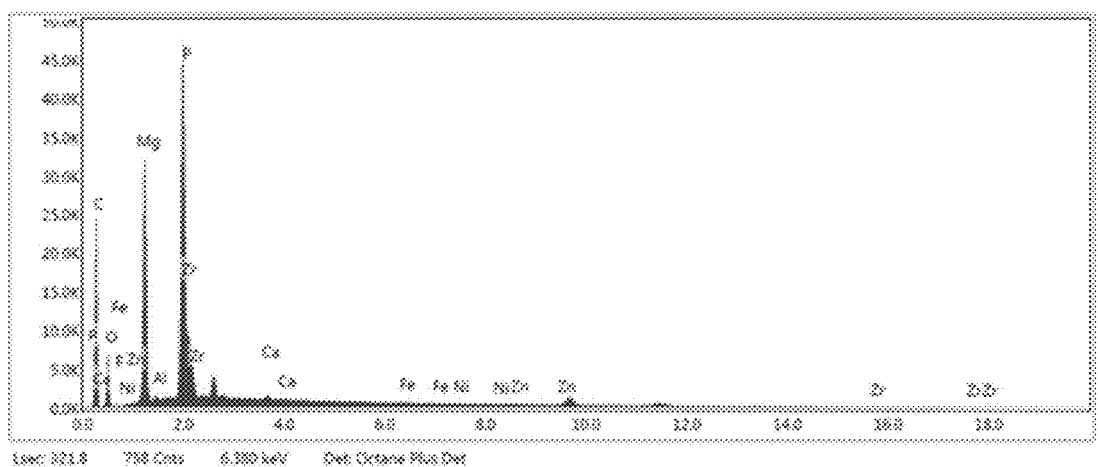

FIG. 9 shows the results of the EDS analysis using eZAF Smart Quant for two different phases of the PEO coated Mg alloy ZX00. In the bottom an exemplary EDS spectrum (here for the phase P K/MgK/C K) is shown.

Figure 10:
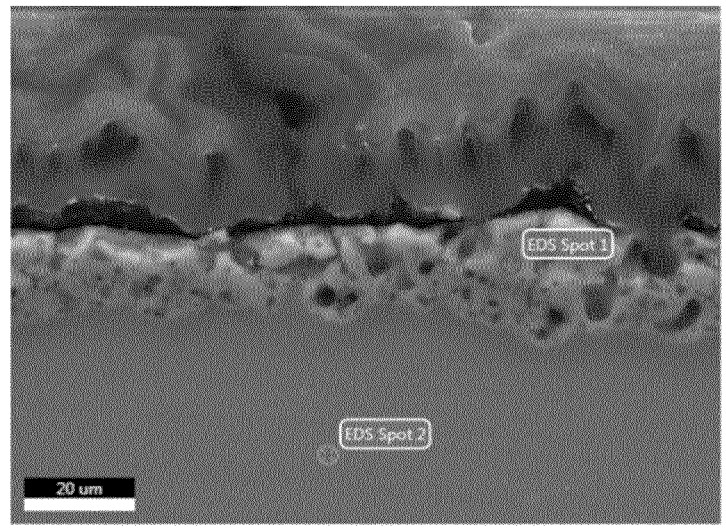

FIG. 10 shows the cross section of the PEO coated ZX00 Mg alloy with selection of two different EDS spots, for which the elemental composition as determined by eZAF Smart Quant is shown below.

Figure 11:
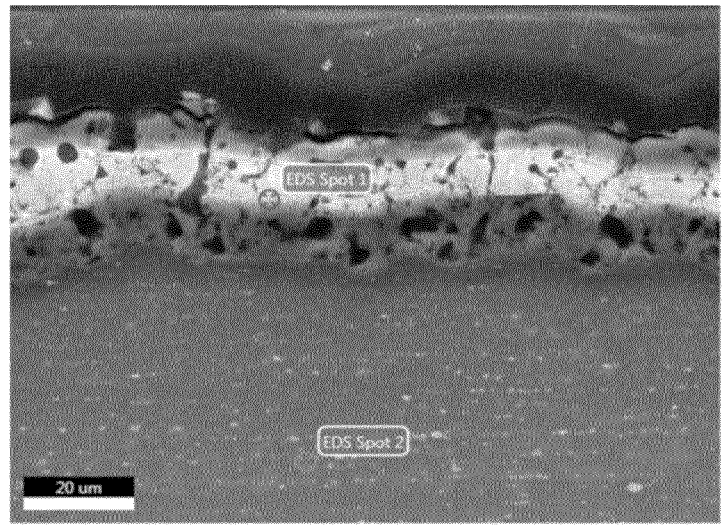

FIG. 11 shows the cross section of the PEO coated WE43 Mg alloy with selection of two different EDS spots, for which the elemental composition as determined by eZAF Smart Quant is shown below.

Figure 12:
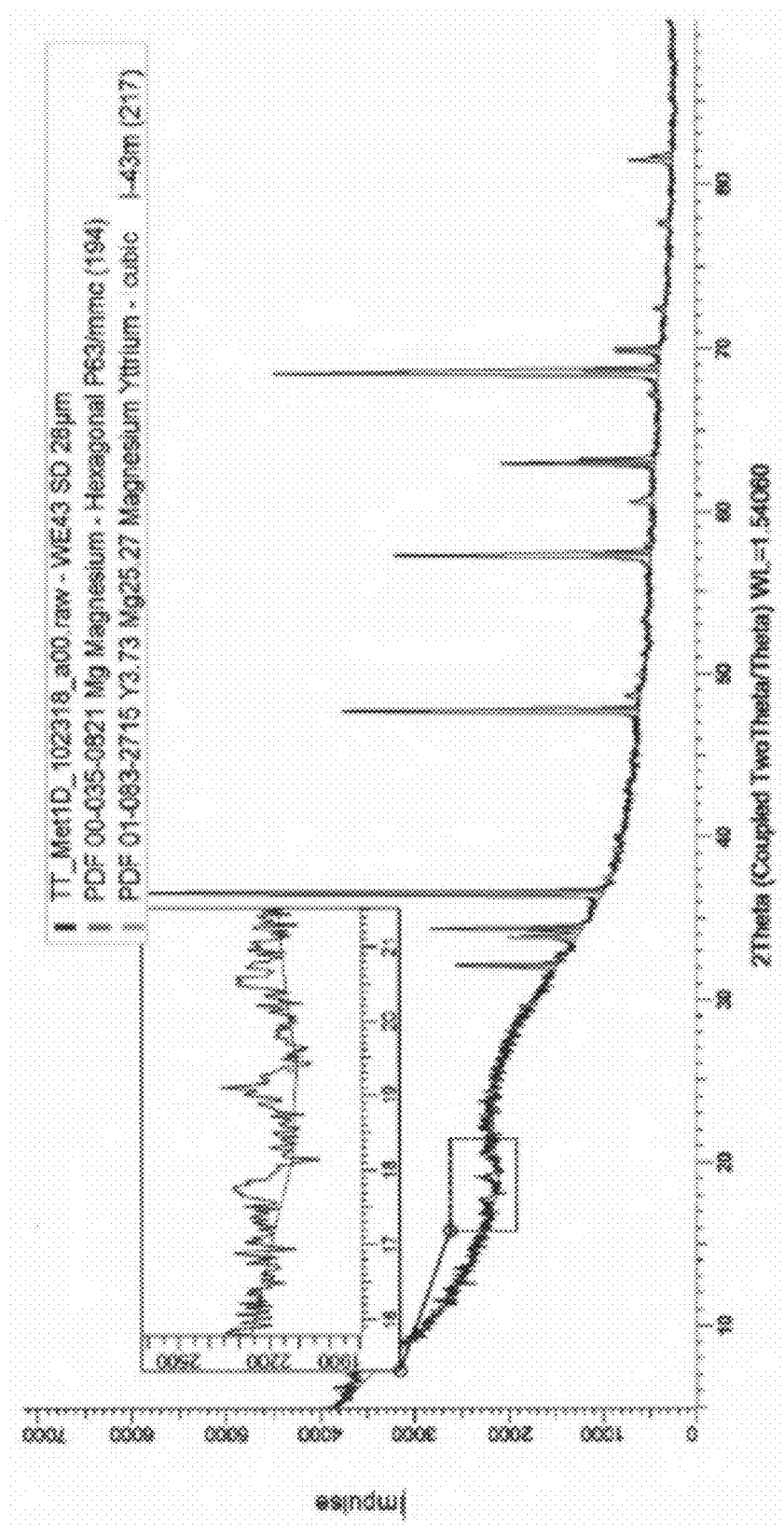
Figure 13:
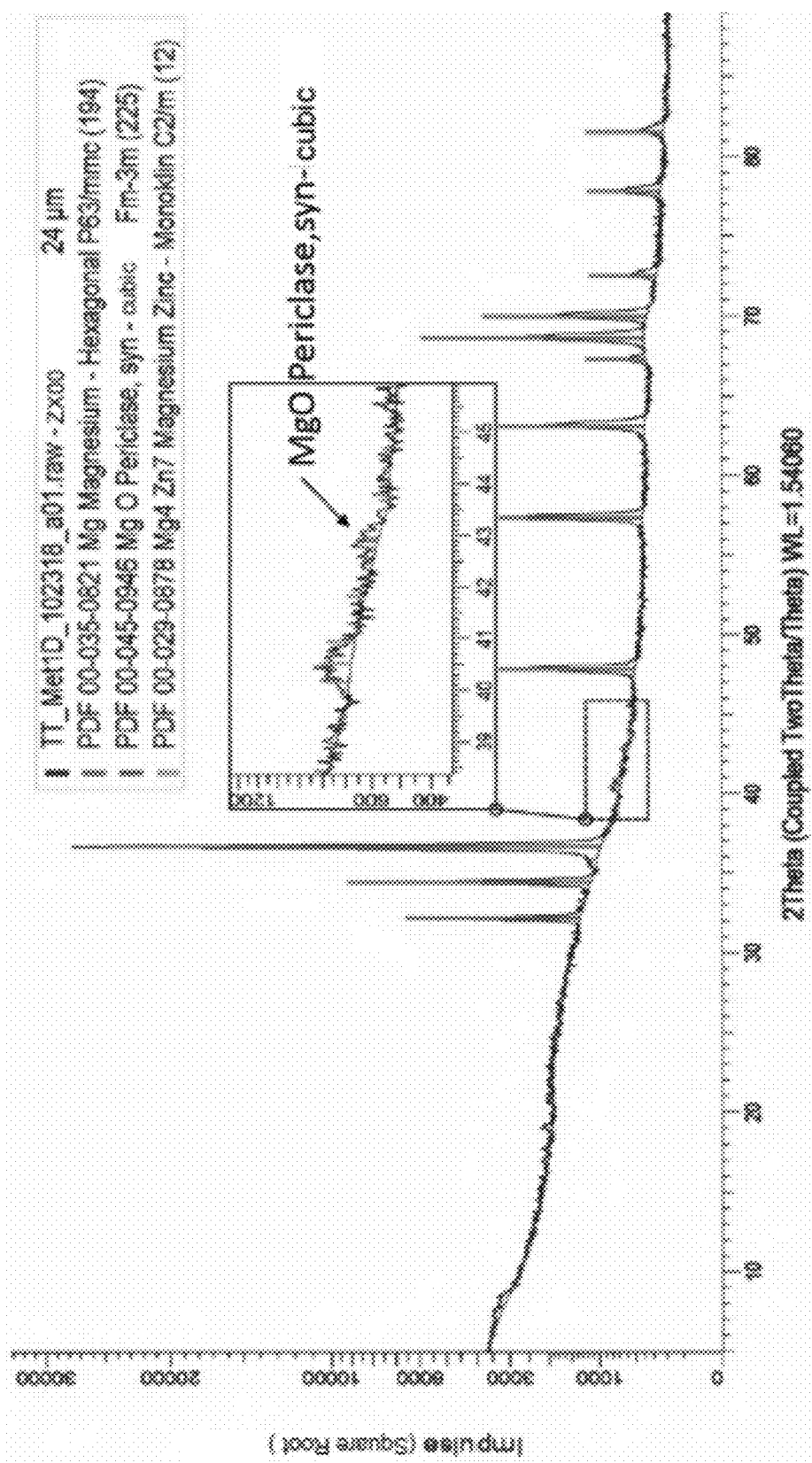

FIGS. 12 and 13 show the results of the x-ray crystallographic analysis for an PEO-coated Mg alloys with two different impulse presentations.

Figure 14:
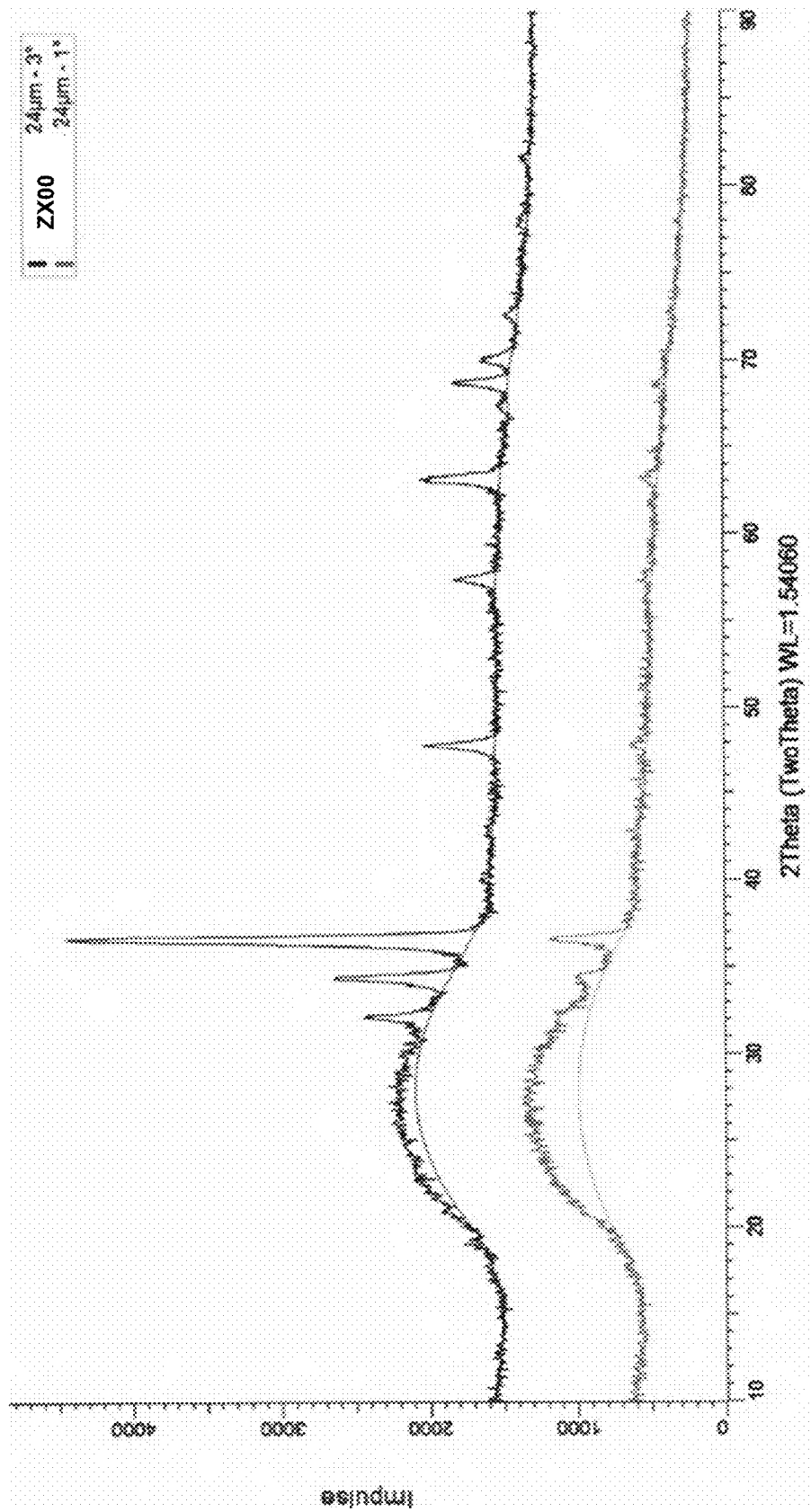
Figure 15:
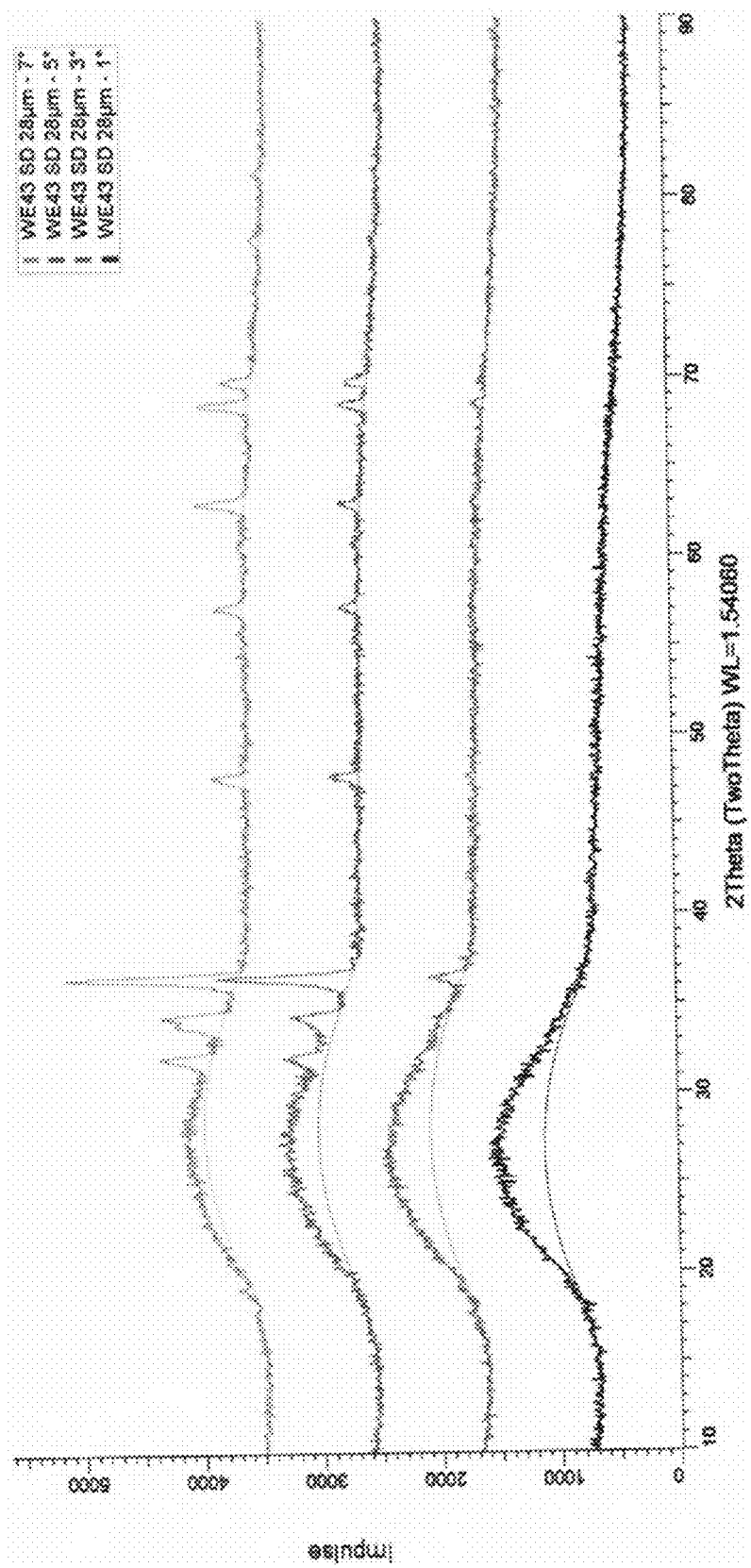
Figure 16:
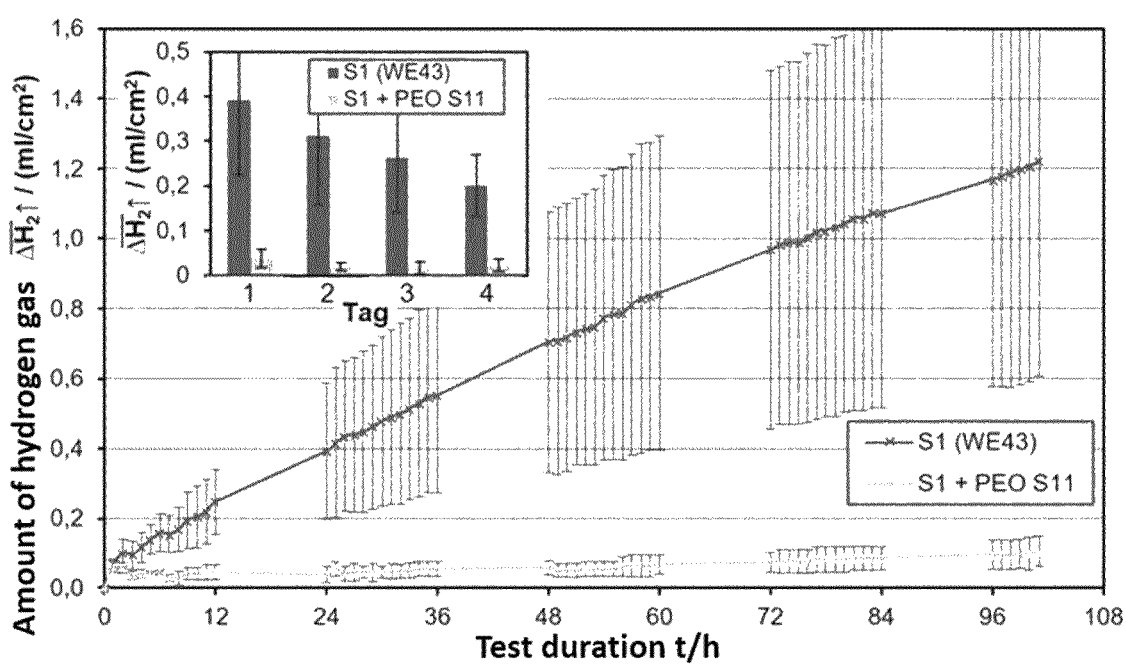

FIGS. 14 and 15 show the results of the x-ray crystallographic analysis for an PEO-coated Mg alloy WE43 and ZX00 under different angles.

Figure 17:
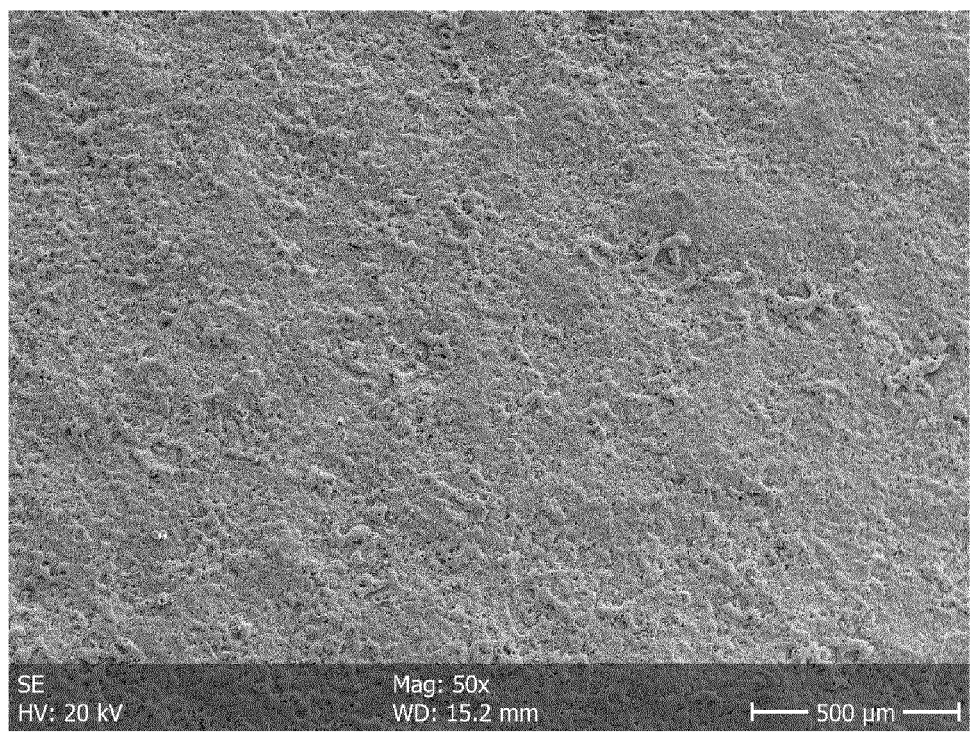
Figure 18:
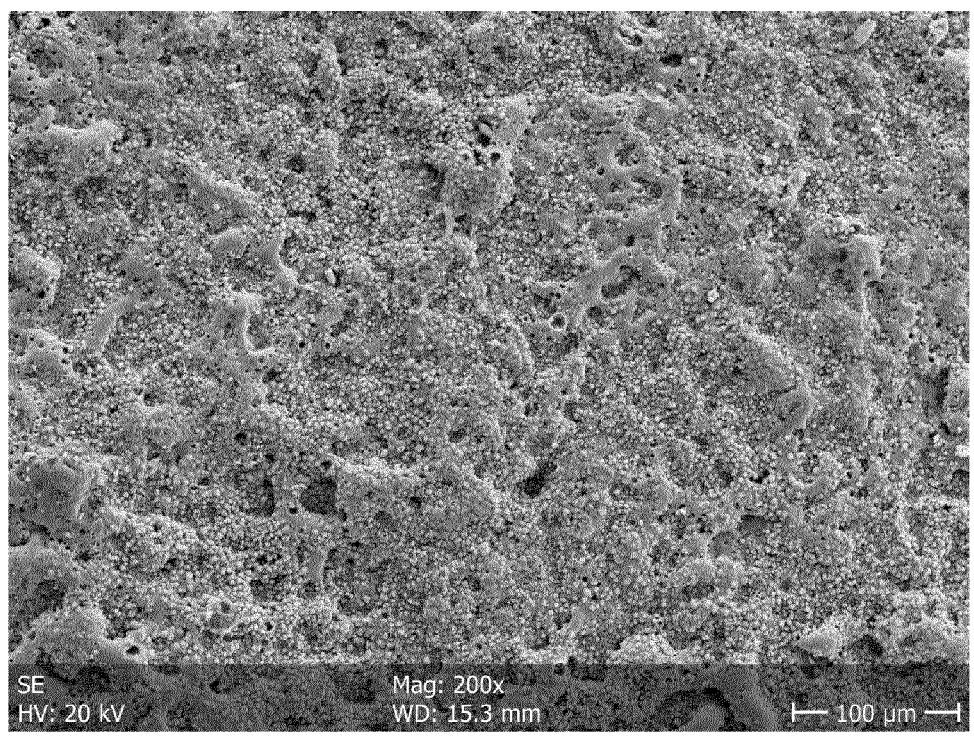
Figure 19:
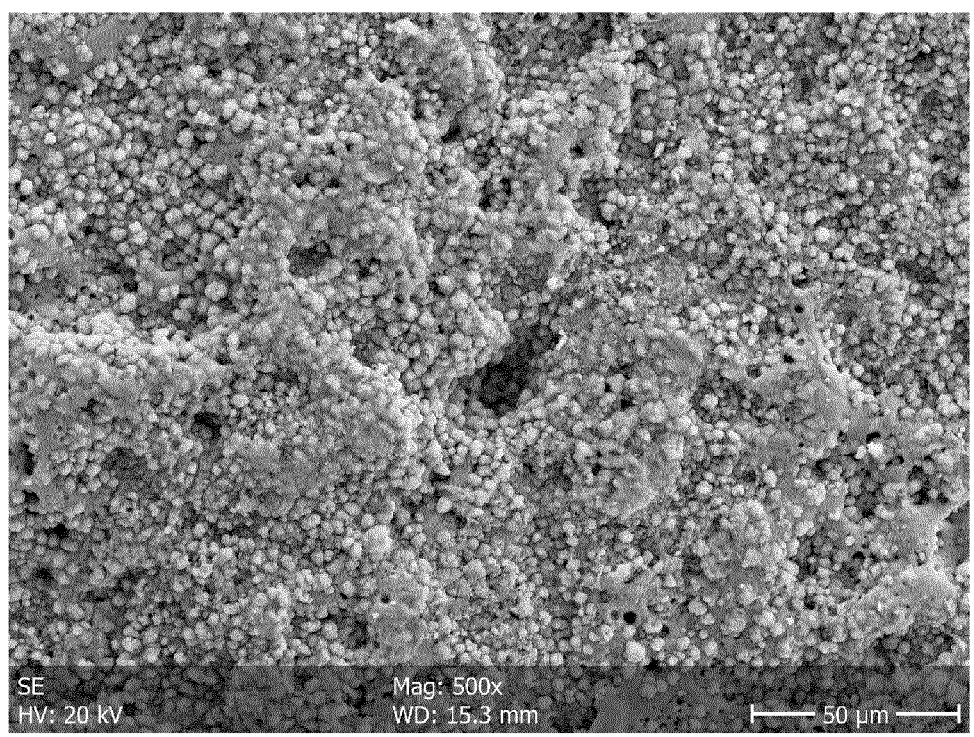

FIGS. 17, 18 and 19 show the surface of a PEO coated Zn1Mg specimen (1 wt-% Magnesium, remainder is Zinc) analysed with scanning-electron microscopy (SEM). FIG. 17 depicts the surface in small, FIG. 18 in middle and FIG. 19 in high magnification. A typical PEO coating can be observed comprising an open porosity on top of the surface and in this case also small coating spheres additionally bound to the surface.

Figure 20:
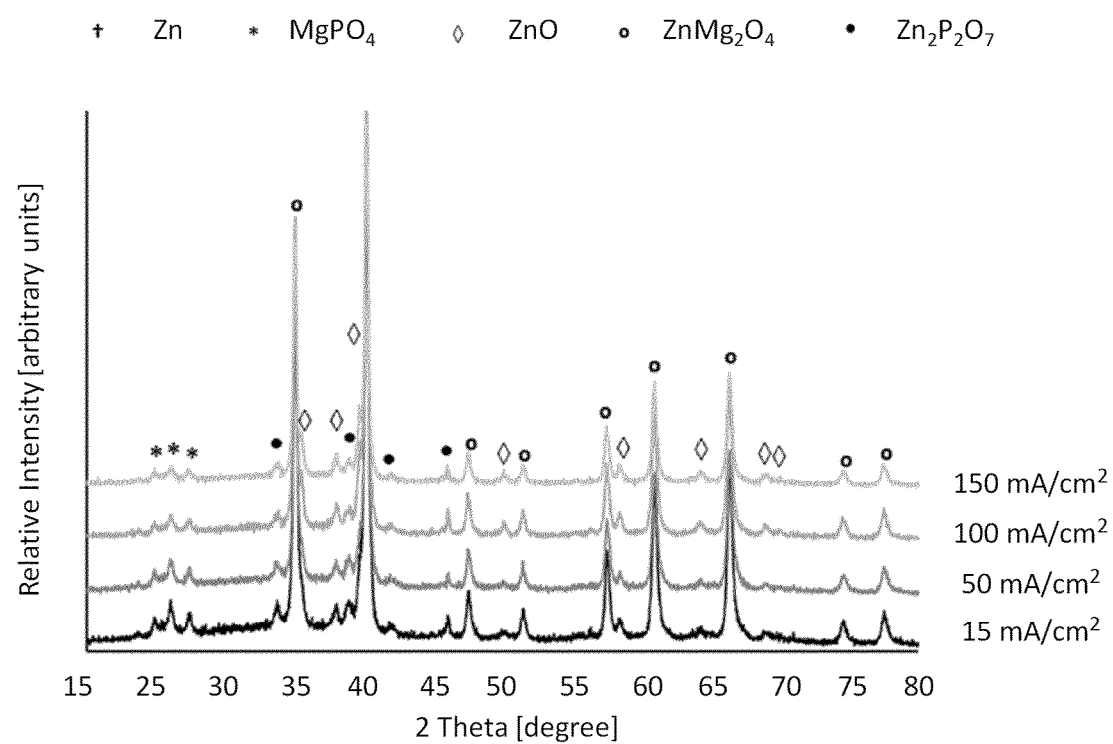

FIG. 20 shows the phase composition of an exemplary resulting PEO coating on Zn1MG specimen (1 wt-% Magnesium, remainder is Zinc) in dependency of the applied current densities using Phosphate and KOH containing electrolyte. The phase composition was characterized using a Bruker D8 Advances XRD at room temperature. Ni-filtered Cu Kα radiation was used. Following settings were applied during the measurements: 0.02° step size, 2 s dwell time, 3° glancing angle and 20 $s_{-1}$ sample rotation rate. Apparently different Phosphates and Oxides further containing entities of the base materials (Magnesium and Zinc) could be created during conversion of the surface and determined by the measurements. Thus, being in accordance with the present invention.

In the Figures, like numbers refer to like objects throughout. Objects in the Figures are not necessarily drawn to scale.

DETAILED DESCRIPTION OF EMBODIMENTS

Various embodiments of the invention will now be described by means of the Figures.

Figure 1:
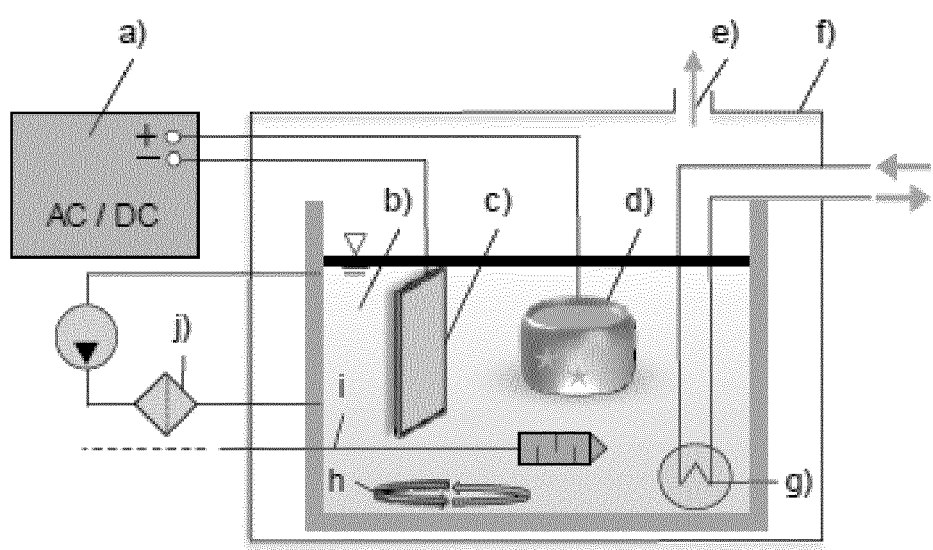

FIG. 1 shows a principal sketch of the PEO cell for coating of the Mg alloy products. The electrolyte circulation helps to removes gas bubbles from the surface of the Mg alloy product, which might impair the growth of a homogenous layer. By blowing in fine air bubbles (i) the laminar boundary layer will be removed continuously so that an increased exchange with the electrolyte is achieved.

Definitions

The term "biodegradable" as used in the context of the present invention refers to a device that is degradable under physiological conditions.

The term "biodegradation" as used herein for the degradation of the implant within the organism of the recipient is synonymous to the terms "degradation", "absorption", "resorption", "corrosion" and "biocorrosion".

The term "plasma anodisation" as used herein is synonymous to the following terms: "anodic sparc oxidation (ANOF)", "microarc oxidation (MAO)", "anodic spark deposition (ASD)", "microplasma oxidation (MPO)", "plasma chemical oxidation (PCO)" and "micro-arc discharge oxidation (MDO)".

In the context of the present application the term coating also encompasses the conversion of surface material and surface modification.

A used herein, the terms "spark discharge" and "plasma discharge" are synonymous terms.

The term oxide as used in the context of the present invention encompasses also oxide-hydrates.

The term "phosphate" as used herein denotes to phosphates, diphosphates and polyphosphates.

As used herein, a metal phosphate is a chemical compound of a metal and at least one phosphate being a chemical derivative of a phosphoric acid. A phosphoric acid is hereby defined as a proton-donating phosphor-oxygen compound and thereby encompasses all types of HxPyOz compounds, such as orthophosphoric acid, metaphosphoric acid, polyphosphoric acid, phosphonic acid and phosphorous acid.

In the context of the present invention a metal oxide is a chemical compound containing at least one oxygen atom and a metal cation as further element. Examples are MgO, ZnO, CaO, $ZrO_2$, or ZnO.

Of note, a change in quantity of atoms within an entity in the surface layer either consisting of oxygen, phosphate or a metal is considered a different substance. For example, ZnO and $ZnO_2$ will be considered different substances, as they exhibit a different amount of oxygen atoms. In another example, $ZnO_2$ and $ZnMgO_2$ will be considered different substances, as they exhibit different amounts of magnesium atoms. The absence of an element in this sense will be considered as having a quantity of 0.

Of note, a "rare earth element" is an element selected from the list consisting of Y, Sc, La, Ce, Pr, Nd, Pm, Sm, Eu, Gd, Tb, Dy, Ho, Er, Tm, Yb, Lu or any other element being considered a rare earth by general technical knowledge as also described in standard text books.

Of note, the term "coated on its surface" refers to the fact that at least one part of the surface of the implant is coated.

As used in the context of the invention, the term "biocompatible" relates to a device that is substantially non-toxic in an in vivo environment, and is not substantially rejected by a recipient's physiological system.

LIST OF REFERENCE NUMERALS a) power source
b) electrolyte solution
c) counter electrode
d) mg ally test piece
e) gas aspiration
f) encapsulation
g) heat exchanger
h) electrolyte circulation
i) air supply
j) filter

The invention claimed is:

1. A biodegradable implant comprising a magnesium or zinc alloy product coated on its surface with a coating layer comprising at least three substances being
   a. a metal oxide of a metal selected from rare-earth elements, Mg, Ca, Zn, Zr, Cu, Sr, Li, Mn or Ag; and/or
   b. a metal phosphate of a metal selected from rare-earth elements, Mg, Ca, Zn, Zr, Cu, Sr, Li, Mn or Ag;
   wherein the magnesium alloy is selected form the group consisting of a magnesium silver alloy (Mg—Ag), a Mg—Y-RE alloy containing yttrium and at least one additional rare earth element (RE), and a magnesium alloy comprising calcium and zinc, or
   wherein the zinc alloy is a selected from the group consisting of a zinc-magnesium alloy with the addition of calcium (Zn—Ca—Mg or Zn—Mg—Ca), a zinc-silver alloy (Zn—Ag) with or without the addition of magnesium (Zn—Ag—Mg or Zn—Mg—Ag), a zinc-strontium alloy with the addition of magnesium (Zn—Sr—Mg or Zn—Mg—Sr), a zinc-lithium alloy with or without the addition of magnesium (Zn—Li—Mg) or (Zi—Mg—Li), a zinc-calcium alloy with the addition of magnesium (Zn—Ca—Mg or Zn—Mg—Ca), and a zinc-manganese alloy (Zn—Mn) with or without the addition of magnesium (Zn—Mn—Mg or Zn—Mg—Mn).

2. The biodegradable implant according to claim 1, wherein the coated magnesium or zinc alloy product comprises the following characteristic: the metal oxide or metal phosphate forms an amorphous domain within the coating layer.

3. The biodegradable implant according to claim 1, wherein the metal oxide or metal phosphate of the coated magnesium or zinc alloy product forms a crystalline domain within the coating layer.

4. The biodegradable implant according to claim 1, wherein the coated magnesium or zinc alloy product comprises the following characteristic: the coating layer has a thickness of between 2 to 50 μm.

5. The biodegradable implant according to claim 1, wherein the coated magnesium or zinc alloy product comprises the following characteristic: the coating layer comprises metal fluorides which increase in their concentration starting from the top surface of the coating layer down to the bottom, alloy-product oriented surface of the coating layer, building a distinct metal fluoride enriched zone at the bottom surface of the coating layer.

6. The biodegradable implant according to claim 1, wherein the coated magnesium or zinc alloy product comprises the following characteristic: the top surface of the coating layer has a mean Vickers hardness from 150 to 800 as measured according to DIN EN ISO 6507-1/4:2018.

7. The biodegradable implant according to claim 1, wherein the coated magnesium or zinc alloy product comprises the following characteristic: the coating layer is generated by plasma electrolytic oxidation.

8. The biodegradable implant according to claim 1, wherein the coating layer is manufactured by a conversion coating.

9. The biodegradable implant according to claim 1, wherein the coating layer is a porous layer, wherein pores at the top of the porous layer have a mean pore size of between 0.1 to 10 μm².

10. The biodegradable implant according to claim 9, wherein the pores have a mean pore size of between 2 to 8 μm².

11. The biodegradable implant according to claim 1, wherein the Mg—Y-RE alloy is a Mg—Y—Nd with or without addition of Zr and the magnesium alloy comprising calcium and zinc is Mg—Ca—Zn or Mg—Zn—Ca alloy with or without addition of Zr.

12. The biodegradable implant according to claim 1, wherein the coated magnesium or zinc alloy product after incubation for 100 hours in Minimal Essential Medium at 37° C. under non-turbulent stirring has a hydrogen gas evolution rate of less than 1.0 ml/cm², as measured by continuous volumetric measurement of the generated hydrogen gas.

13. The biodegradable implant of claim 4, wherein the coating layer has a thickness of between 5 to 35 μm.

14. The biodegradable implant of claim 10, wherein the pores have a mean pore size of 4 to 6 μm.

15. The biodegradable implant of claim 11, wherein the magnesium alloy is a Mg—Y—Nd alloy with a Y content between 3 and 5 wt. %.

16. The biodegradable implant of claim 11, wherein the magnesium alloy comprising calcium and zinc is a Mg—

Ca—Zn or Mg—Zn—Ca alloy with or without the addition of Zr and having Ca and Zn contents each below 1 wt. %.

17. The biodegradable implant of claim 12, wherein the coated magnesium or zinc alloy product after incubation for 100 hours in Minimal Essential Medium at 37° C. under non-turbulent stirring has a hydrogen gas evolution rate of less than 0.6 ml/cm$^2$ as measured by continuous volumetric measurement of the generated hydrogen gas.

18. The biodegradable implant of claim 12, wherein the coated magnesium or zinc alloy product after incubation for 100 hours in Minimal Essential Medium at 37° C. under non-turbulent stirring has a hydrogen gas evolution rate of less than 0.2 ml/cm$^2$ as measured by continuous volumetric measurement of the generated hydrogen gas.

* * * * *